United States Patent [19]

Narr et al.

[11] Patent Number: 5,684,029
[45] Date of Patent: *Nov. 4, 1997

[54] BENZIMIDAZOLES, PHARMACEUTICAL COMPOSITIONS CONTAINING THESE COMPOUNDS AND PROCESSES FOR PREPARING THEM

[75] Inventors: Berthold Narr; Norbert Hauel, both of Biberach; Jacques Van Meel, Mittelbiberach; Wolfgang Wienen, Apfingen; Michael Entzeroth, Warthausen; Uwe Ries, Biberach, all of Germany

[73] Assignee: Karl Thomae GmbH, Biberach, Germany

[*] Notice: The term of this patent shall not extend beyond the expiration date of Pat. No. 5,591,702.

[21] Appl. No.: 603,773

[22] Filed: Feb. 20, 1996

Related U.S. Application Data

[62] Division of Ser. No. 299,693, Sep. 1, 1994, which is a division of Ser. No. 220,472, Mar. 30, 1994, Pat. No. 5,385,925, which is a continuation of Ser. No. 732,868, Jul. 19, 1991, abandoned.

[30] Foreign Application Priority Data

| Jul. 23, 1990 | [DE] | Germany | 40 23 369.3 |
| Oct. 4, 1990 | [DE] | Germany | 40 31287.9 |
| Feb. 20, 1991 | [DE] | Germany | 41 05 324.0 |

[51] Int. Cl.$^6$ ............... A61K 31/415; C07D 403/10; C07D 403/14
[52] U.S. Cl. ............... 514/394; 514/381; 548/250; 548/253; 548/305.4
[58] Field of Search ............... 514/394, 381; 548/305.4, 250, 253

[56] References Cited

U.S. PATENT DOCUMENTS

| 5,385,925 | 1/1995 | Narr et al. | 514/382 |
| 5,591,762 | 1/1997 | Hauel et al. | 514/381 |

*Primary Examiner*—Yogendra N. Gupta
*Attorney, Agent, or Firm*—Robert P. Raymond; Alan R. Stempel; Wendy E. Rieder

[57] ABSTRACT

The invention relates to benzimidazoles of general formula

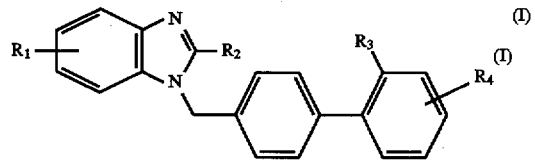

wherein
$R_1$ to $R_4$ are as defined herein, the 1-, 3-isomer mixtures thereof and the addition salts thereof. The new compounds are useful, in particular, as angiotensin antagonists.

8 Claims, No Drawings

BENZIMIDAZOLES, PHARMACEUTICAL COMPOSITIONS CONTAINING THESE COMPOUNDS AND PROCESSES FOR PREPARING THEM

This is a division of application Ser. No. 08/299,693, filed Sep. 1, 1994, which is a division of application Ser. No. 08/220,472, filed Mar. 30, 1994, now U.S. Pat. No. 5,385,925, which is a continuation of application of application Ser. No. 07/732,868, filed Jul. 19, 1991, now abandoned.

U.S. Pat. No. 4,880,804 describes inter alia 4'-[(2-alkylbenzimidazol-1-yl)-methyl]biphenyl-2-carboxylic acids and 4'-[(2-alkyl-benzimidazol-1-yl)-methyl]-2-(1H-tetrazol-5-yl)-biphenyls which are substituted in the benzimidazole ring by an alkanoylaminomethyl group and which are angiotension-II antagonists.

It has now been found that the new benzimidazoles of general formula

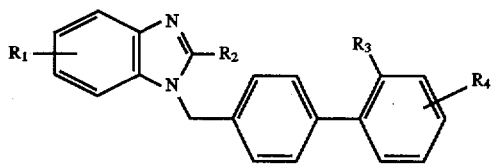

the 1,3-isomer mixtures and addition salts thereof, particularly, for pharmaceutical use, the physiologically acceptable addition salts thereof with organic or inorganic acids or bases, are even more useful angiotensin antagonists, particularly angiotensin-II antagonists.

In the general formula above:

$R_1$ represents a tetrahydrobenzimidazolyl or imidazopyridinyl group or a benzimidazolyl or benzoxazolyl group optionally substituted in the phenyl nucleus by a fluorine, chlorine or bromine atom, by a $C_{1-3}$-alkyl group, by a $C_{1-3}$-alkoxy group or by a trifluoromethyl group, whilst the NH group of the above-mentioned imidazole rings may additionally be substituted by a $C_{1-6}$-alkyl group or by a $C_{3-7}$-cycloalkyl group, an amino group substituted by a bicyclohexylcarbonyl or biphenylcarbonyl group or a hydroxycycloalkylamino carbonyl group having 5 to 7 carbon atoms in the cycloalkyl moiety, which may additionally be substituted at the N-atom by a $C_{1-3}$-alkyl group, an aminocarbonylamino group substituted by a bicyclohexyl or biphenyl group and optionally also substituted by one or two $C_{1-3}$alkyl groups at the N-atom, with the exception of the 2-oxo-3,4-tetramethylene-pyrrolidin-1-yl group a 5-, 6- or 7-membered alkyleneimino or alkenyleneimino group optionally substituted by one or two $C_{1-3}$-alkyl groups or by a tetramethylene or pentamethylene group, in which a methylene group is replaced by a carbonyl or sulphonyl group, a 3,4,5,6-tetrahydro-2(1H)-pyrimidinone group optionally substituted by an alkyl or phenylalkyl group each having 1 to 3 carbon atoms in the alkyl moiety, a straight-chained or branched hydroxyalkylamino carbonyl group having 4 to 6 carbon atoms in the alkyl moiety, a maleic acid amido or maleic acid imido group optionally mono- or disubstituted by a $C_{1-3}$-alkyl or by a phenyl group, in which the substituents may be identical or different, an imidazoline or imidazole group optionally substituted by a $C_{1-6}$-alkyl group or by a $C_{3-7}$-cycloalkyl group, an imidazolidinedione group optionally substituted by a $C_{1-3}$-alkyl group, by a phenylalkyl group having 1 to 3 carbon atoms in the alkyl moiety or by a tetramethylene, pentamethylene or hexamethylene group, a $C_{1-6}$-alkylsulphonyloxy group, a benzenesulphonyloxy group optionally substituted by a $C_{1-3}$-alkyl group, an alkylamino or phenylalkylamino group substituted by a $C_{4-6}$-alkylsulphonyl group or by a phenylalkylsulphonyl group,
wherein the alkyl moiety in each case may contain from 1 to 3 carbon atoms, an amino or alkylamino group substituted by a naphthalenesulphonyl group, which may be substituted in the naphthalene ring by a dialkylamino group or by one or two alkoxy groups, whilst the alkyl moiety in each case may contain from 1 to 3 carbon atoms, a $C_{3-5}$-alkoxy group which is substituted in the 3-, 4- or 5-position by an imidazolyl group, a $C_{2-5}$-alkoxy group which is substituted in the 2-, 3-, 4- or 5-position by a benzimidazolyl or tetrahydro-benzimidazolyl group, a pyridazin-3-one or dihydro-pyridazin-3-one group which may be substituted in the 2-position by an optionally phenyl-substituted $C_{1-3}$alkyl group and additionally in the carbon structure by 1 or 2 alkyl groups having 1 to 3 carbon atoms, a pyrrolidino, piperidino or hexamethyleneimino group substituted by two $C_{1-3}$-alkyl groups, a 7-nitrobenzofurazan-4-yl-aminoalkanoylamino group in which the alkanoyl moiety may contain 2 or 3 carbon atoms, a heptamethyleneimino, 1H,3H-quinazolin-2,4-dion-3-yl, pentamethylene-oxazolin-2-yl, benzofuran-carbonylamino or 7-nitro-benzofurazan-4-yl-amino group or, if $R_3$ represents a carboxy group and $R_2$ represents an n-butyl group, $R_1$ in the 6-position represents an amino group substituted by a phenylsulphonyl, cyclohexylmethylaminocarbonyl, 2-carboxycyclohexyl-methylcarbonyl, 2-tert.butoxycarbonyl-cyclohexylmethyl-carbonyl, 2-carboxy-3,4,5,6-tetrahydrobenzoyl, N-methyl-phenylaminocarbonyl or 3-cyclohexylpropyl group, a methylamino group substituted by a propylsulphonyl, phenylsulphonyl, methylphenylsulphonyl or chlorophenyl-sulphonyl group, an n-pentylamino group substituted by a phenylsulphonyl or methoxyphenylsulphonyl group, an n-propylamino group substituted by a methylphenylsulphonyl or methoxyphenylsulphonyl group, an isopropylamino group substituted by a benzoyl or chlorophenylsulphonyl group, an N-acetyl-cyclohexylmethylamino, 3,4,5,6-tetrahydrophthalimido, hexahydrohomophthalimido, N-methanesulphonyl-2-phenylethylamino, N-chlorophenyl-sulphonyl-benzylamino, piperidino, 4-methyl-piperidino or hexamethyleneimino group or, if $R_3$ represents a carboxy group and $R_2$ represents an n-butyl group, $R_1$ in the 5- or 6-position represents a 2-oxo-1,2-dihydro-3,4-tetramethylene-pyrrolidin-1-yl, 3-carboxy-propionyl or 3-carboxy-2-methyl-propionyl group or, if $R_3$ represents a carboxy group and $R_2$ represents a methyl, ethyl, n-propyl, n-butyl or methylmercapto group, $R_1$ in the 6-position represents a pyrrolidino-carbonylamino group or, if $R_3$ represents a tetrazolyl group and $R_2$ represents an n-butyl group, $R_1$ in the 5- or 6-position represents an n-pentylamino group substituted by a methyl-aminocarbonyl or cyclohexylaminocarbonyl group or in the 6-position represents a 3,3-dimethyl-glutaric acid imido or 4,4-tetramethylene-glutaric acid imido group, or, if $R_3$ represents a tetrazolyl group and $R_2$ represents an ethyl or n-propyl group, $R_1$ in the 6-position represents an N-benzenesulphonyl-methylamino group or, if $R_3$ represents a tert.butoxycarbonyl group and $R_2$ represents an n-butyl group, $R_1$ in the 6-position represents a 2-carboxycyclohexylmethylcarbonylamino or pyrrolidinocarbonylamino group, $R_2$ represents a hydrogen atom or a straight-chained or branched $C_{1-5}$-alkyl group in which a methylene group may be replaced by a sulphur atom, $R_3$ represents a carboxy, cyano, 1H-tetrazolyl or 1-triphenylmethyl-tetrazolyl group or an alkoxycarbonyl group with a total of 2 to 5 carbon atoms and $R_4$ represents a hydrogen, fluorine, chlorine or bromine atom.

The present invention thus relates to the new above-mentioned benzimidazoles, whilst the corresponding cyano, tert.-butoxycarbonyl and triphenylmethyl compounds in particular represent valuable intermediate products.

Thus, the present invention also relates to new pharmaceutical compositions which contain one of the above-mentioned pharmacologically active compounds of general formula I or a corresponding physiologically acceptable salt and are suitable particularly for the treatment of hypertension and cardiac insufficiency and also for treating ischaemic peripheral circulatory disorders, myocardial ischaemia (angina), for the prevention of the progression of cardiac insufficiency after myocardial infarct and for treating diabetic nephropathy, glaucoma, gastrointestinal diseases and bladder diseases.

As examples of the definitions of groups $R_1$ and $R_2$ mentioned hereinbefore:

$R_1$ may represent a benzimidazol-2-yl, 1-methyl-benzimidazol-2-yl, 1-ethyl-benzimidazol-2-yl, 1-n-propyl-benzimidazol-2-yl, 1-isopropyl-benzimidazol-2-yl, 1-n-butyl-benzimidazol-2-yl, 1-n-pentyl-benzimidazol-2-yl, 1-n-hexyl-benzimidazol-2-yl, 1-cyclopropyl-benzimidazol-2-yl, 1-cyclopentyl-benzimidazol-2-yl, 1-cyclohexyl-benzimidazol-2-yl, 1-cycloheptyl-benzimidazol-2-yl, 1,5-dimethyl-benzimidazol-2-yl, 1,6-dimethyl-benzimidazol-2-yl, 1-methyl-5-methoxy-benzimidazol-2-yl, 1-methyl-5-fluoro-benzimidazol-2-yl, 1-methyl-5-chloro-benzimidazol-2-yl, 1-methyl-5-bromo-benzimidazol-2-yl, 1-methyl-5-trifluoromethyl-benzimidazol-2-yl, tetrahydro-benzimidazol-2-yl, 1-methyl-tetrahydro-benzimidazol-2-yl, 1-ethyl-tetrahydro-benzimidazol-2-yl, 1-n-propyl-tetrahydro-benzimidazol-2-yl, 1-isopropyl-tetrahydro-benzimidazol-2-yl, 1-n-butyl-tetrahydro-benzimidazol-2-yl, 1-n-pentyl-tetrahydro-benzimidazol-2-yl, 1-n-hexyl-tetrahydro-benzimidazol-2-yl, 1-cyclopropyl-tetrahydro-benzimidazol-2-yl, 1-cyclopentyl-tetrahydro-benzimidazol-2-yl, 1-cyclohexyl-tetrahydro-benzimidazol-2-yl, 1-cycloheptyl-tetrahydro-benzimidazol-2-yl, benzoxazol-2-yl, 5-methyl-benzoxazol-2-yl, 5-methoxy-benzoxazol-2-yl, 5-trifluoromethyl-benzoxazol-2-yl, 5-fluoro-benzoxazol-2-yl, 5-chloro-benzoxazol-2-yl, 5-bromo-benzoxazol-2-yl, 4-biphenylyl-carbonylamino, 4-cyclohexylcarbonylamino, N-methyl-4-biphenylylcarbonylamino, N-ethyl-4-cyclohexylcarbonylamino, N-n-propyl-4-biphenylylcarbonylamino, N-isopropyl-4-cyclohexylcarbonylamino, 2-hydroxycyclopentylamino, 2-hydroxy-cyclohexylamino, 2-hydroxy-cycloheptylamino, 3-hydroxy-cyclopentylamino, 3-hydroxy-cyclohexylamino, 3-hydroxy-cycloheptylamino, 4-hydroxy-cyclohexylamino, 4-hydroxy-cycloheptylamino, N-methyl-2-hydroxy-cyclopentylamino, N-ethyl-2-hydroxy-cyclohexylamino, N-isopropyl-2-hydroxy-cycloheptylamino, N-methyl-3-hydroxy-cyclopentylamino, N-ethyl-3-hydroxy-cyclohexylamino, N-n-propyl-3-hydroxy-cycloheptylamino, N-methyl-4-hydroxy-cyclohexylamino, N-ethyl-4-hydroxy-cycloheptylamino, 4-biphenylylaminocarbonylamino, 4-bicyclohexylaminocarbonylamino, N-(4-biphenylylaminocarbonyl)-methylamino, N-(4-bicyclohexylaminocarbonyl)-methylamino, N-(methyl-4-biphenylylaminocarbonyl)-methylamino, N-(methyl-4-bicyclohexylaminocarbonyl)-methylamino, N-(4-biphenylylaminocarbonyl)-ethylamino, N-(4-bicyclohexylaminocarbonyl)-isopropylamino, N-(ethyl-4-biphenylylaminocarbonyl)-methylamino, N-(methyl-4-bicyclohexylaminocarbonyl)-ethylamino, pyrrolidin-2-on-1-yl, piperidin-2-on-1-yl, hexamethyleneimino-2-on-1-yl, propanesultam-1-yl, butanesultam-1-yl, pentanesultam-1-yl, 3,4,5,6-tetrahydro-2(1H)-pyrimidon-1-yl, 3-methyl-3,4,5,6-tetrahydro-2(1H)-pyrimidon-1yl, 3-ethyl-3,4,5,6-tetrahydro-2(1H)-pyrimidon-1-yl, 3-n-propyl-3,4,5,6-tetrahydro-2(1H)-pyrimidon-1-yl, 3-isopropyl-3,4,5,6-tetrahydro-2(1H)-pyrimidon-1-yl, 3-benzyl-3,4,5,6-tetrahydro-2(1H)-pyrimidon-1-yl, 3-(2-phenylethyl)-3,4,5,6-tetrahydro-2(1H)-pyrimidon-1-yl, 3-(3-phenylpropyl)-3,4,5,6-tetrahydro-2(1H)-pyrimidon-1-yl, 4-hydroxybutylamino, 5-hydroxypentylamino, 6-hydroxyhexylamino, maleic acid imido, 2-methyl-maleic acid imido, 2-phenyl-maleic acid imido, 2,3-dimethyl-maleic acid imido, 2,3-diphenyl-maleic acid imido, 2-methyl-maleic acid amido, 3-methyl-maleic acid amido, 2,3-dimethyl-maleic acid amido, 2-phenyl-maleic acid amido, 3-phenyl-maleic acid amido, 2,3-diphenyl-maleic acid amido, 3-methyl-2-phenyl-maleic acid amido, 2-methyl-3-phenyl-maleic acid amido, imidazolin-2-yl, 1-methyl-imidazolin-2-yl, 1-ethyl-imidazolin-2-yl, 1-propyl-imidazolin-2-yl, imidazolidin-2,4-dion-3-yl, 5-methyl-imidazolidin-2,4-dion-3-yl, 5-ethyl-imidazolidin-2,4-dion-3-yl, 5-n-propyl-imidazolidin-2,4-dion-3-yl, 5-benzyl-imidazolidin-2,4-dion-3-yl, 5-(2-phenylethyl)-imidazolidin-2,4-dion-3-yl, 5-(3-phenylpropyl)-imidazolidin-2,4-dion-3-yl, 5,5-tetramethylene-imidazolidin-2,4-dion-3-yl, 5,5-pentamethylene-imidazolidin-2,4-dion-3-yl, 5,5-hexamethylene-imidazolidin-2,4-dion-3-yl, 5,5-dimethyl-imidazolidin-2,4-dion-3-yl, 5,5-diethyl-imidazolidin-2,4-dion-3-yl, methanesulphonyloxy, ethanesulphonyloxy, propanesulphonyloxy, butanesulphonyloxy, pentanesulphonyloxy, hexanesulphonyloxy, benzenesulphonyloxy, p-toluenesulphonyloxy, N-n-butanesulphonyl-methylamino, N-n-pentanesulphonyl-methylamino, N-n-hexanesulphonyl-methylamino, N-phenylmethanesulphonyl-methylamino, N-(2-phenylethanesulphonyl)-methylamino, N-(3-phenylpropanesulphonyl)-methylamino, N-n-butanesulphonyl-ethylamino, N-n-pentanesulphonyl-isopropylamino, N-n-hexanesulphonyl-ethylamino, N-phenylmethanesulphonyl-ethylamino, N-(2-phenylethanesulphonyl)-n-propylamino, N-(3-phenylpropanesulphonyl)-ethylamino, naphthalen-1-sulphonylamino, naphthalen-2-sulphonylamino, 5-dimethylamino-naphthalen-1-sulphonylamino, N-(naphthalen-1-sulphonyl)-methylamino, N-(naphthalen-2-sulphonyl)-ethylamino, N-(5-dimethylamino-naphthalen-1-sulphonyl)-methylamino, N-(5-methoxynaphthalen-1-sulphonyl)-methylamino, N-(5,6-dimethoxy-naphthalen-2-sulphonyl)-ethylamino, 3-(imidazol-1-yl)-propoxy, 4-(imidazol-1-yl)-butoxy, 5-(imidazol-1-yl)-pentoxy, 2-(benzimidazol-1-yl)-ethoxy, 3-(benzimidazol-1-yl)-propoxy, 4-(benzimidazol-1-yl)-butoxy, 5-(benzimidazol-1-yl)-pentoxy, 2-(tetrahydrobenzimidazol-1-yl)-ethoxy, 3-(tetrahydrobenzimidazol-1-yl)-propoxy, 4-(tetrahydrobenzimidazol-1-yl)-butoxy, 5-(tetrahydrobenzimidazol-1-yl)-pentoxy, 4,5-dihydro- 2H-pyridazin-3-on-6-yl, 2-methyl-4,5-dihydro-2H-pyridazin-3-on-6-yl, 2-ethyl-4,5-dihydro-2H-pyridazin-3-on-6-yl, 2-n-propyl-4,5-dihydro-2H-pyridazin-3-on-6-yl, 2-isopropyl-4,5-dihydro-2H-pyridazin-3-on-6-yl, 2-benzyl-4,5-dihydro-2H-pyridazin-3-on-6-yl, 2-(2-phenylethyl)-4,5-dihydro-2H-pyridazin-3-on-6-yl, 2-(3-phenylpropyl)-4,5-dihydro-2H-pyridazin-3-on-6-yl, 4-methyl-4,5-dihydro-2H-pyridazin-3-on-6-yl, 5-methyl-4,5-dihydro-2H-pyridazin-3-on-6-yl, 4,4-dimethyl-4,5-dihydro-2H-pyridazin-3-on-6-yl, 5,5-dimethyl-4,5-dihydro-2H-pyridazin-3-on-6-yl, 4,5-dimethyl-4,5-dihydro-2H-pyridazin-3-on-6-yl, 2,4-dimethyl-4,5-dihydro-2H-pyridazin-3-on-6-yl, 2,5-dimethyl-4,5-dihydro-2H-pyridazin-3-on-6-yl, 2,4,5-trimethyl-4,5-dihydro-2H-pyridazin-3-on-6-yl, 2,4,4-trimethyl-4,5-dihydro-2H-pyridazin-3-on-6-yl, 2,5,5-trimethyl-4,5-dihydro-2H-pyridazin-3-on-6-yl, 2H-pyridazin-3-on-6-yl, 2-methyl-2H-pyridazin-3-on-6-yl, 2-ethyl-2H-pyridazin-3-on-6-yl, 2-n-propyl-2H-pyridazin-3-on-6-yl, 2-isopropyl-2H-pyridazin-3-on-6-yl, 2-benzyl-2H-pyridazin-3-on-6-yl, 2-(2-phenylethyl)-2H-pyridazin-3-on-6-yl, 2-(3-phenylpropyl)-2H-pyridazin-3-on-6-yl, 4-methyl-2H-pyridazin-3-on-6-yl, 5-methyl-2H-pyridazin-3-on-6-yl, 4,5-dimethyl-2H-pyridazin-3-on-6-yl, 2,4-dimethyl-2H-pyridazin-3-on-6-yl, 2,5-dimethyl-2H-pyridazin-3-on-6-yl, 2,4,5-trimethyl-2H-pyridazin-3-on-6-yl, 3,3-dimethyl-pyrrolidino, 3,4-dimethylpyrrolidino, 3,3-dimethyl-piperidino, 3,4-dimethylpiperidino, 4,4-dimethyl-piperidino, 3,3-dimethyl-hexamethyleneimino, 3,4-dimethyl-hexamethyleneimino, 4,4-dimethylhexa-methyleneimino, 3,5-dimethyl-hexamethyleneimino, phenylsulphonylamino, cyclohexylmethylaminocarbonylamino, 2-methylaminobenzoylamino, 2-carboxy-cyclohexylmethylcarbonylamino, 2-tert.butoxycarbonylcyclohexylmethylcarbonylamino, 2-carboxy-3,4,5,6-tetrahydrobenzoylamino, 3-cyclohexylpropylamino, N-propylsulphonylmethylamino, N-phenylsulphonylmethylamino, N-(4-methylphenylsulphonyl)-methylamino, N-(4-chlorophenylsulphonyl)-methylamino, N-phenylsulphonyl-n-pentylamino, N-(4-methoxyphenylsulphonyl)-n-pentylamino, N-(4-methylphenylsulphonyl)-n-propylamino, N-(4-methoxyphenylsulphonyl)-n-propylamino, N-benzoylisopropylamino, N-(4-chlorophenylsulphonyl)-isopropylamino, N-acetyl-cyclohexylmethylamino, 3,4,5,6-tetrahydrophthalimido, hexahydrophthalimido, N-methanesulphonyl-2-phenylethylamino, N-chlorophenylsulphonylbenzylamino, piperidino, 4-methyl-piperidino, hexamethyleneimino, 3-carboxy-propionyl, 3-carboxy-2-methyl-propionyl, pyrrolidinocarbonylamino, N-methylaminocarbonyl-n-pentylamino, N-cyclohexylaminocarbonyl-n-pentylamino, 3,3-dimethyl-glutaric acid imido, 4,4-tetramethylene-glutaric acid imido, 2-carboxy-cyclohexylmethylcarbonylamino, 1-n-butyl-imidazolin-2-yl, 1-n-pentyl-imidazolin-2-yl, 1-n-hexyl-imidazolin-2-yl, 1-cyclopropyl-imidazolin-2-yl, 1-cyclobutyl-imidazolin-2-yl, 1-cyclohexyl-imidazolin-2-yl, 1-cycloheptyl-imidazolin-2-yl, imidazol-2-yl, 1-methyl-imidazol-2-yl, 1-ethyl-imidazol-2-yl, 1-propyl-imidazol-2-yl, 1-n-butyl-imidazol-2-yl, 1-n-pentyl-imidazol-2-yl, 1-n-hexyl-imidazol-2-yl, 1-cyclopropyl-imidazol-2-yl, 1-cyclobutyl-imidazol-2-yl, 1-cyclohexyl-imidazol-2-yl or 1-cycloheptyl-imidazol-2-yl group and $R_2$ may represent, for example, a hydrogen atom, a methyl, ethyl, n-propyl, isopropyl, n-butyl, isobutyl, tert.-butyl, n-pentyl, 1-methylpropyl, 1-methylbutyl, 2-methylbutyl, 3-methylbutyl, 1-ethylpropyl, 1,1-diethylethyl, methylmercaptomethyl, 2-methylmercaptoethyl, 3-methylmercaptopropyl or 4-methylmercaptobutyl group.

Preferred compounds of the above general formula are, however, those wherein $R_1$ represents a tetrahydrobenzimidazolyl or imidazopyridinyl group, a benzimidazolyl group optionally substituted in the phenyl nucleus by a fluorine, chlorine or bromine atom or by a methyl, methoxy or trifluoromethyl group, whilst the NH-group of the above-mentioned imidazole rings may additionally be substituted by a $C_{1-6}$-alkyl group or by a $C_{3-6}$-cycloalkyl group, a benzoxazol-2-yl group optionally substituted by a methyl group, an amino group substituted by a bicyclohexylcarbonyl, biphenylcarbonyl or benzofuryl-2-carbonyl group, an aminocarbonylamino group substituted in the 3-position by a bicyclohexyl or biphenyl group, a 5-, 6- or 7-membered alkyleneimino or alkenyleneimino group optionally substituted by one or two methyl groups or by a tetramethylene or pentamethylene group, wherein a methylene group is replaced by a carbonyl or sulphonyl group, a 3,4,5,6-tetrahydro-2(1H)-pyrimidinone group optionally substituted by a methyl or benzyl group, a hydroxyalkylaminocarbonyl group having 4 carbon atoms in the alkyl moiety, a maleic acid amido or maleic acid imido group optionally mono- or disubstituted by a methyl group or by a phenyl group, wherein the substituents may be identical or different, an imidazolin-2-yl or imidazol-2-yl group substituted in the 1-position by a $C_{1-6}$-alkyl group or by a $C_{3-7}$-cycloalkyl group, an imidazolidinedione group optionally substituted by a methyl, benzyl, tetramethylene or pentamethylene group, a methylamino or benzylamino group substituted by a butanesulphonyl group or by a phenylmethanesulphonyl group, an amino or methylamino group substituted by a naphthalenesulphonyl group, which may be substituted in the naphthalene ring by a dimethylamino group or by 2 methoxy groups, a pyridazin-3-one or dihydro-pyridazin-3-one group optionally substituted by a methyl or benzyl group, a pyrrolidino, piperidino or hexamethyleneimino group substituted by two methyl groups, a heptamethyleneimino, 1H,3H-quinazolin-2,4-dion-3-yl, hydroxycyclohexylaminocarbonyl, 4,5-pentamethyleneoxazolin-2-yl, 7-nitrobenzofurazan-4-yl-amino or 7-nitro-benzofurazan-4-yl-aminopropionylamino group or, if $R_3$ represents a carboxy group and $R_2$ represents an n-butyl group, $R_1$ in the 6-position represents an amino group substituted by a phenylsulphonyl, cyclohexylmethylaminocarbonyl, 2-carboxycyclohexylmethylcarbonyl, 2-tert.-butoxycarbonyl-cyclohexylmethylcarbonyl, 2-carboxy-3,4,5,6-tetrahydrobenzoyl, N-methyl-phenylaminocarbonyl or 3-cyclohexylpropyl group, a methylamino group substituted by a propylsulphonyl, phenylsulphonyl, 4-methylphenylsulphonyl or 4-chlorophenylsulphonyl group, an n-pentylamino group substituted by a phenylsulphonyl or 4-methoxyphenylsulphonyl group, an n-propylamino group substituted by a 4-methylphenylsulphonyl or 4-methoxyphenylsulphonyl group, an isopropylamino group substituted by a benzoyl or 4-chlorophenylsulphonyl group, an N-acetylcyclohexylmethylamino, 3,4,5,6-tetrahydrophthalimido, hexahydrohomophthalimido, N-methanesulphonyl-2-phenylethylamino, N-(4-chlorophenylsulphonyl)-benzylamino, piperidino, 4-methyl-piperidino or hexamethyleneimino group or, if $R_3$ represents a carboxy group and $R_2$ represents an n-butyl group, $R_1$ in the 5- or 6-position represents a 2-oxo-1,2-dihydro-3,4-tetramethylene-pyrrolidin-1-yl, 3-carboxy-propionyl or 3-carboxy-2-methyl-propionyl group or, if $R_3$ represents a carboxy group and $R_2$ represents a methyl, ethyl, n-propyl, n-butyl or methylmercapto group, $R_1$ in the 6-position represents a pyrrolidinocarbonylamino group or, if $R_3$ represents a tetrazolyl group and $R_2$ represents an n-butyl group, $R_1$ in the 5- or 6-position represents an n-pentylamino group substituted by a methylaminocarbonyl or cyclohexylaminocarbonyl group or, in the 6-position, a 3,3-dimethyl-glutaric acid imido or 4,4-tetramethylene-glutaric acid imido group, or, if $R_3$ represents a tetrazolyl group and $R_2$ represents an ethyl or n-propyl group, $R_1$ in the 6-position represents an N-benzenesulphonyl-methylamino group or, if $R_3$ represents a tert.butoxycarbonyl group and $R_2$ represents an n-butyl group, $R_1$ in the 6-position represents a 2-carboxy-cyclohexylmethylcarbonylamino or pyrrolidinocarbonylamino group, $R_2$ represents a hydrogen atom or a straight-chained or branched $C_{1-4}$-alkyl group in which a methylene group may be replaced by a sulphur atom, $R_3$ represents a carboxy, cyano, 1H-tetrazolyl or 1-triphenylmethyl-tetrazolyl group or an alkoxycarbonyl group with a total of 2 to 5 carbon atoms and $R_4$ represents a hydrogen, fluorine, chlorine or bromine atom, the 1-, 3-isomer mixtures thereof and the physiologically acceptable salts thereof with organic or inorganic acids or bases.

However, particularly preferred compounds of general formula I above are those wherein $R_1$ in the 6-position represents a 1-methylbenzimidazol-2-yl, 3,4,5,6-tetrahydro-phthalimino, 2,3-diphenyl-maleic acid imido, 2,3-dimethyl-maleic acid imido, N-phenyl-methanesulphonyl-methylamino, 2-oxo-pyrrolidin-1-yl, 2-oxo-piperidin-1-yl, 2-oxo-hexamethyleneimino, 2-oxo-3,4-tetramethylene-pyrrolidin-2-yl, 3,3-dimethylglutarimido, N-methylaminocarbonyl-n-pentylamino, propanesultam-1-yl or butanesultam-1-yl group, $R_2$ represents a methyl, ethyl, n-propyl or n-butyl group, $R_3$ represents a carboxy or 1H-tetrazolyl group and $R_4$ represents a hydrogen atom, and the physiologically acceptable salts thereof with organic or inorganic acids or bases.

According to the invention, the compounds are obtained by the following processes:

a) Cyclising a compound of general formula

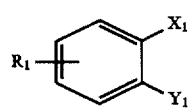

(II)

wherein $R_1$ is defined as hereinbefore, one of the groups $X_1$ or $Y_1$ represents a group of general formula

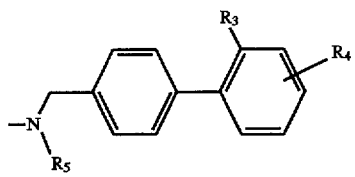

and the other group $X_1$ or $Y_1$ represents a group of the general formula

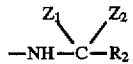

wherein $R_2$ to $R_4$ are defined as hereinbefore, $R_5$ represents a hydrogen atom or an $R_2CO$ group, wherein $R_2$ is defined as hereinbefore, $Z_1$ and $Z_2$, which may be identical or different, represent optionally substituted amino groups or hydroxy or mercapto groups optionally substituted by lower alkyl groups or $Z_1$ and $Z_2$ together represent an oxygen or sulphur atom, an imino group optionally substituted by a $C_{1-3}$-alkyl group, or a $C_{2-3}$-alkylenedioxy or $C_{2-3}$alkylenedithio group, but one of the groups $X_1$ or $Y_1$ must represent a group of general formula

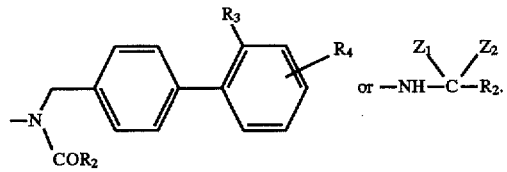

The cyclisation is conveniently carried out in a solvent or mixture of solvents such as ethanol, isopropanol, glacial acetic acid, benzene, chlorobenzene, toluene, xylene, glycol, glycolmonomethylether, diethyleneglycoldimethylether, sulpholane, dimethylformamide, tetraline or in an excess of the acylating agent used to prepare the compound of general formula II, e.g. in the corresponding nitrile, anhydride, acid halide, ester or amide, e.g. at temperatures between 0° and 250° C., but preferably at the boiling temperature of the reaction mixture, optionally in the presence of a condensing agent such as phosphorusoxychloride, thionylchloride, sulphurylchloride, sulphuric acid, p-toluenesulphonic acid, methanesulphonic acid, hydrochloric acid, phosphoric acid, polyphosphoric acid, acetic anhydride or optionally in the presence of a base such as potassium ethoxide or potassium tert.-butoxide. However, cyclisation may also be carried out without a solvent and/or condensing agent.

However, it is particularly advantageous to carry out the reaction by preparing a compound of general formula II in the reaction mixture by reducing a corresponding o-nitroamino compound, optionally in the presence of a carboxylic acid of general formula $R_2COOH$, or by acylation of a corresponding o-diamino compound. When the reduction of the nitro group is broken off at the hydroxylamine stage, the N-oxide of a compound of general formula I is obtained in the subsequent cyclisation. The resulting N-oxide is then converted by reduction into a corresponding compound of general formula I.

The subsequent reduction of the N-oxide of formula I obtained is preferably carried out in a solvent such as water, water/ethanol, methanol, glacial acetic acid, ethyl acetate or dimethylformamide with hydrogen in the presence of a hydrogenation catalyst such as Raney nickel, platinum or palladium/charcoal, with metals such as iron, tin or zinc in the presence of an acid such as acetic, hydrochloric or sulphuric acid, with salts such as iron(II)sulphate, tin(II) chloride or sodium dithionite, or with hydrazine in the presence of Raney nickel at temperatures between 0° and 50° C., but preferably at ambient temperature.

b) Reaction of a benzimidazole of general formula

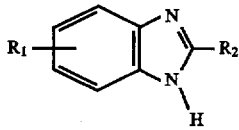

wherein $R_1$ and $R_2$ are defined as hereinbefore, with a biphenyl compound of general formula

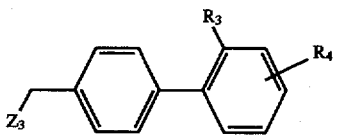

wherein $R_3$ and $R_4$ are defined as hereinbefore and $Z_3$ represents a nucleophilic leaving group such as a halogen atom, e.g. a chlorine, bromine or iodine atom, or a substituted sulphonyloxy group, e.g. a methanesulphonyloxy, phenylsulphonyloxy or p-toluenesulphonyloxy group.

The reaction is conveniently carried out in a solvent or mixture of solvents such as methylene chloride, diethylether, tetrahydrofuran, dioxane, dimethylsulphoxide, dimethylformamide or benzene, optionally in the presence of an acid binding agent such as sodium carbonate, potassium carbonate, sodium hydroxide, potassium tert.-butoxide, triethylamine or pyridine, whilst the latter two may simultaneously also be used as solvent, preferably at temperatures between 0° and 100° C., e.g. at temperatures between ambient temperature and 50° C.

In the reaction, a mixture of the 1 and 3 isomers is preferably obtained which can if desired subsequently be resolved into the corresponding 1 and 3 isomers, preferably by chromatography using a substrate such as silica gel or aluminium oxide.

c) In order to prepare a compound of general formula I wherein $R_3$ represents a carboxy group:

Converting a compound of general formula

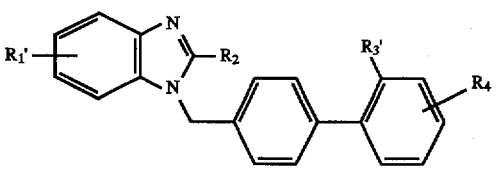

wherein $R_2$ and $R_4$ are defined as hereinbefore, $R_1'$ has the meanings given for $R_1$ hereinbefore and may represent a 3-alkoxycarbonylpropionyl or 3-alkoxycarbonyl-2-methylpropionyl group in which the alkoxy part may contain from 1 to 3 carbon atoms, and $R_3'$ represents a group which may be converted into a carboxy group by hydrolysis, thermolysis or hydrogenolysis.

For example, functional derivatives of the carboxy group such as the unsubstituted or substituted amides, esters, thiolesters, orthoesters, iminoethers, amidines or anhydrides, the nitrile group or the tetrazolyl group may be converted by hydrolysis into a carboxy group, esters with tertiary alcohols, e.g. the tert.butylester, may be converted by thermolysis into a carboxy group and esters with aralkanols, e.g. the benzylester, may be converted by hydrogenolysis into a carboxy group.

The hydrolysis is appropriately carried out either in the presence of an acid such as hydrochloric, sulphuric, phosphoric, trichloroacetic or trifluoroacetic acid or in the presence of a base such as sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture. When hydrolysis is carried out in the presence of an organic acid such as trichloroacetic or trifluoroacetic acid, any alcoholic hydroxy groups present may simultaneously be converted into a corresponding acyloxy group such as the trifluoroacetoxy group.

If $R_3'$ in a compound of general formula V represents a cyano or aminocarbonyl group, these groups may also be converted into the carboxy group with a nitrite, e.g. sodium nitrite, in the presence of an acid such as sulphuric acid, which may simultaneously also be used as solvent, at temperatures between 0° and 50° C.

If $R_3'$ in a compound of general formula V represents for example the tert.-butyloxycarbonyl group, the tert.-butyl group may also be thermally cleaved, optionally in an inert solvent such as methylene chloride, chloroform, benzene, toluene, tetrahydrofuran or dioxane and preferably in the presence of a catalytic amount of an acid such as p-toluenesulphonic acid, sulphuric, phosphoric or polyphosphoric acid, preferably at the boiling temperature of the solvent used, e.g. at temperatures between 40° C. and 100° C.

If $R_3'$ in a compound of general formula V represents the benzyloxycarbonyl group, for example, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 5 bar. During hydrogenolysis, other groups may be reduced at the same time, e.g. a nitro group may be reduced to the amino group, a benzyloxy group to the hydroxy group, a vinylidene group to the corresponding alkylidene group or a cinnamic acid group to the corresponding phenyl-propionic acid group, or they may be replaced by hydrogen atoms, e.g. a halogen may be replaced by a hydrogen atom.

If $R_1$ in a compound of general formula V represents one of the above mentioned hydrolysable groups, it may be converted during the reaction into a corresponding carboxy or amino compound.

d) In order to prepare a compound of general formula I wherein $R_3$ represents a 1H-tetrazolyl group:

Cleaving of a protecting group from a compound of general formula

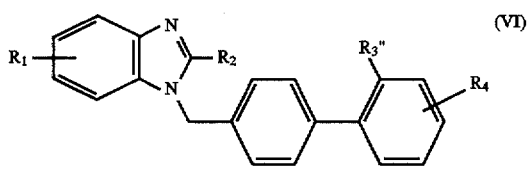

(VI)

wherein

R$_1$, R$_2$ and R$_4$ are defined as hereinbefore and

R$_3$" represents a 1H-tetrazolyl group protected in the 1- or 3-position by a protecting group.

Suitable protecting groups include, for example, the triphenylmethyl, tributyl tin or triphenyl tin groups.

The cleaving of a protecting group used is preferably carried out in the presence of a hydrohalic acid, preferably in the presence of hydrochloric acid, in the presence of a base such as sodium hydroxide or alcoholic ammonia in a suitable solvent such as methylene chloride, methanol, methanol/ammonia, ethanol or isopropanol at temperatures between 0° and 100° C., but preferably at ambient temperature or, if the reaction is carried out in the presence of alcoholic ammonia, at elevated temperatures, e.g. at temperatures between 100° and 150° C., preferably at temperatures between 120° and 140° C.

e) In order to prepare a compound of general formula I wherein R$_3$ represents a 1H-tetrazolyl group:

Reaction of a compound of general formula

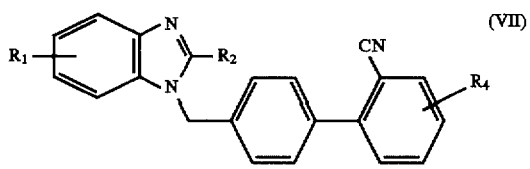

(VII)

wherein

R$_1$, R$_2$ and R$_4$ are defined as hereinbefore, with hydrazoic acid or the salts thereof.

The reaction is preferably carried out in a solvent such as benzene, toluene or dimethylformamide at temperatures between 80° and 150° C., preferably at 125° C. Appropriately, either the hydrazoic acid is liberated during the reaction from an alkali metal azide, e.g. sodium azide, in the presence of a weak acid such as ammonium chloride or the tetrazolide salt obtained in the reaction mixture during the reaction with a salt of hydrazoic acid, preferably with aluminium azide or tributyl tin azide, which is also preferably produced in the reaction mixture by reacting aluminium chloride or tributyl tin chloride with an alkali metal azide such as sodium azide, is subsequently liberated by acidification with a dilute acid such as 2N hydrochloric or 2N sulphuric acid.

f) In order to prepare compounds of general formula I wherein R$_1$ represents a pentamethylene-oxazolin-2-yl group:

Reacting a compound of general formula

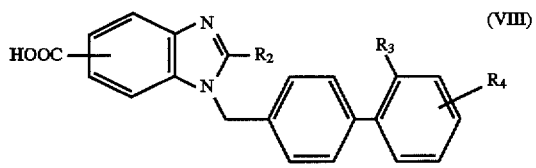

(VIII)

wherein

R$_2$ to R$_4$ are defined as hereinbefore, with 1-aminomethylcyclohexanol in the presence of an acid-activating agent.

The reaction is preferably carried out in a solvent such as tetrahydrofuran or dioxane in the presence of an acid activating agent such as carbonylimidazole at temperatures between 0° and 50° C., preferably at ambient temperature.

g) In order to prepare a compound of general formula I wherein R$_1$ represents a 2-oxo-3,4-tetramethylenepyrrolidin-1-yl group:

Hydrogenation of a compound of general formula

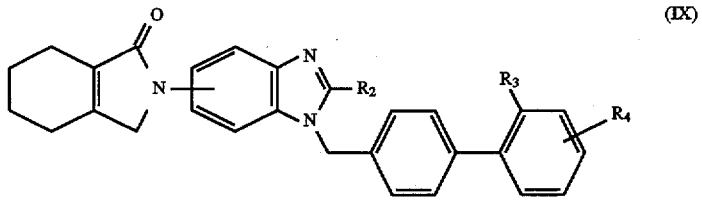

(IX)

wherein

R$_2$, R$_3$ and R$_4$ are defined as hereinbefore.

The catalytic hydrogenation is carried out with hydrogen in the presence of a catalyst such as palladium/charcoal in a solvent such as methanol, ethanol, ethyl acetate or glacial acetic acid at temperatures between 0° and 50° C., but preferably at ambient temperature, under a hydrogen pressure of 1 to 7 bar, but preferably from 3 to 5 bar.

h) In order to prepare compounds of general formula I wherein R$_1$ represents an amino group substituted by a bicyclohexylcarbonyl or biphenylcarbonyl group, which may additionally be substituted at the N-atom by a C$_{1-3}$-alkyl group, an aminocarbonylamino group substituted by a bicyclohexyl or biphenyl group and optionally additionally substituted by one or two C$_{1-3}$alkyl groups at the N-atom, a maleic acid amido or maleic acid imido group optionally mono- or disubstituted by a C$_{1-3}$-alkyl group or by a phenyl group, in which the substituents may be identical or different, an alkylamino or phenylalkylamino group substituted by a C$_{4-6}$-alkylsulphonyl group or by a phenylalkylsulphonyl group, wherein the alkyl moiety may contain 1 to 3 carbon atoms, an amino or alkylamino group substituted by a naphthalenesulphonyl group and optionally substituted in the naphthalene ring by a dialkylamino group or by one or two alkoxy groups, whilst the alkyl moiety may contain 1 to 3 carbon atoms, a 7-nitro-benzofurazan-4-yl-aminoalkanoylamino group wherein the alkanoyl moiety may contain 2 or 3 carbon atoms, a benzofurancarbonylamino or 7-nitro-benzofurazan-4-yl-amino group or, if R$_3$ represents a carboxy group and R$_2$ represents an n-butyl group, R$_1$ in the 6-position represents an amino group substituted by a phenylsulphonyl, cyclohexylmethylamino-carbonyl, 2-carboxycyclohexylmethylcarbonyl, 2-tert.-butoxycarbonylcyclohexylmethylcarbonyl, 2-carboxy-3,4,5,6-tetrahydrobenzoyl, N-methyl-phenylaminocarbonyl or 3-cyclohexylpropyl group, a methylamino group substituted by a propylsulphonyl, phenylsulphonyl, methylphenylsulphonyl or chlorophenylsulphonyl group, an n-pentylamino group substituted by a phenylsulphonyl or methoxyphenylsulphonyl group, an n-propylamino group substituted by a methylphenylsulphonyl or methoxyphenylsulphonyl group, an isopropylamino group substituted by a benzoyl or chlorophenylsulphonyl group, an N-acetylcyclohexylmethylamino, 3,4,5,6-tetrahydrophthalimido, hexahydrohomophthalimido, N-methanesulphonyl-2-phenylethylamino or N-chlorophenylsulphonyl-benzylamino group or, if $R_3$ represents a carboxy group and $R_2$ represents an n-butyl group, $R_1$ in the 5- or 6-position represents a 2-oxo-1,2-dihydro-3,4-tetramethylene-pyrrolidin-1-yl group or, if $R_3$ represents a carboxy group and $R_3$ represents a methyl, ethyl, n-propyl, n-butyl or methylmercapto group, $R_1$ in the 6-position represents a pyrrolidinocarbonylamino group or, if $R_3$ represents a tetrazolyl group and $R_2$ represents an n-butyl group, $R_1$ in the 5- or 6-position represents an n-pentylamino group substituted by a methylaminocarbonyl or cyclohexylaminocarbonyl group or in the 6-position represents a 3,3-dimethylglutaric acid imido or 4,4-tetramethylene-glutaric acid imido group, or, if $R_3$ represents a tetrazolyl group and $R_2$ represents an ethyl or n-propyl group, $R_1$ in the 6-position represents an N-benzenesulphonyl-methylamino group or, if $R_3$ represents a tert.-butoxycarbonyl group and $R_2$ represents an n-butyl group, $R_1$ in the 6-position represents a 2-carboxy-cyclohexylmethylcarbonylamino or pyrrolidinocarbonylamino group:

Reacting a compound of general formula

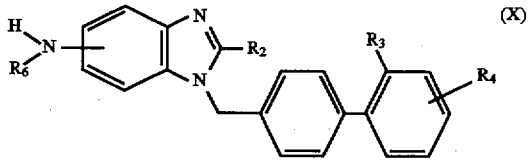

(X)

wherein $R_2$, $R_3$ and $R_4$ are defined as hereinbefore and $R_6$ represents a hydrogen atom, an n-pentyl, cyclohexylmethyl, alkyl or phenylalkyl group each having 1 to 3 carbon atoms in the alkyl moiety, with a compound of general formula

(XI)

wherein $Z_4$ represents a nucleophilic leaving group,

W represents a —CO— or —SO$_2$— group and $R_7$ represents a 2-hydroxycarbonyl-ethenyl group wherein the ethenyl moiety is mono- or disubstituted by a $C_{1-3}$-alkyl group or by a phenyl group and the substituents may be identical or different, a $C_{3-6}$-alkyl group, a phenylalkyl group having 1 to 3 carbon atoms in the alkyl moiety, a naphthalene group optionally substituted by a dialkylamino group or by one or two alkoxy groups, wherein each alkyl moiety may contain from 1 to 3 carbon atoms, a methyl, phenyl, methylphenyl, methoxyphenyl, chlorophenyl, biphenyl, bicyclohexyl, 2-carboxy-cyclohexylmethyl, 2-carboxy-3,4,5,6-tetrahydrophenyl, 3-carboxy-1,1-dimethyl-propyl, 3-carboxy-2,2-tetramethylenepropyl, 7-nitro-benzofurazan-4-yl-aminomethyl or 7-nitro-benzofurazan-4-yl-aminoethyl group, or, if W represents a —CO— group, an $R_8NR_9$ group wherein $R_8$ represents a hydrogen atom or a $C_{1-3}$-alkyl group, $R_9$ represents a methyl, cyclohexyl, cyclohexylmethyl, phenyl, biphenyl or bicyclohexyl group or $R_8$ and $R_9$ together with the nitrogen atom between them represent a pyrrolidino group or $Z_4$ together with $R_9$ represents another carbon-nitrogen bond, or $R_7$ together with W represents a 7-nitro-benzofurazan-4-yl-amino group.

Examples of nucleophilic leaving groups for $Z_4$ include the chlorine or bromine atoms, an alkoxy or phenylalkoxy group such as a methoxy, ethoxy or benzyloxy group or, if $R_7$ represents one of the above-mentioned hydrocarbon groups, a hydroxy group.

The reaction is conveniently carried out in a solvent such as methylene chloride, chloroform, carbon tetrachloride, ether, tetrahydrofuran, dioxane, benzene, toluene, acetonitrile or dimethylformamide, optionally in the presence of an acid activating agent or a dehydrating agent, e.g. in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, or an agent which activates the amino group, e.g. phosphorus trichloride, and optionally in the presence of an inorganic base such as sodium carbonate or a tertiary organic base such as triethylamine or pyridine, which may simultaneously be used as solvents, at temperatures between $-25°$ and $150°$ C., but preferably at temperatures between $-10°$ C. and the boiling temperature of the solvent used.

If $Z_4$ represents a hydroxy group, however, it is particularly advantageous to carry out the reaction with the reactive derivatives of a carboxylic acid of general formula IX, e.g. with the esters, thioesters, halides, anhydrides or imidazolides.

i) In order to prepare compounds of general formula I wherein $R_1$ represents a tetrahydrobenzimidazolyl or imidazopyridinyl group or a benzimidazolyl group optionally substituted in the phenyl nucleus by a fluorine, chlorine or bromine atom, by a $C_{1-3}$-alkyl group, by a $C_{1-3}$-alkoxy group or by a trifluoromethyl group, whilst the NH-group of the above-mentioned imidazole rings may additionally be substituted by a $C_{1-6}$-alkyl group or by a $C_{3-7}$-cycloalkyl group, a hydroxycycloalkylaminocarbonyl group having 5 to 7 carbon atoms in the cycloalkyl moiety, which may additionally be substituted at the N-atom by a $C_{1-3}$-alkyl group, or a straight-chained or branched hydroxyalkylaminocarbonyl group having 4 to 6 carbon atoms in the alkyl moiety:

Reaction of a compound of general formula

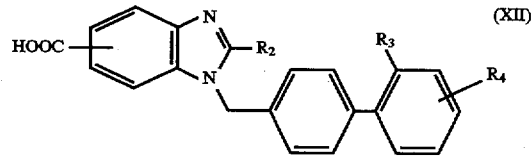

(XII)

wherein $R_2$ to $R_4$ are defined as hereinbefore, or the reactive derivatives thereof such as the acid halides, esters, amides, anhydrides or nitriles thereof, with an amine of general formula

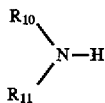 (XIII)

wherein $R_{10}$ represents a hydrogen atom, a cycloalkyl group or a $C_{1-6}$-alkyl group and $R_{11}$ represents a $C_{4-6}$-hydroxyalkyl group, a $C_{5-7}$-hydroxycycloalkyl group or a 2-aminophenyl group which may be substituted in the phenyl nucleus by a fluorine, chlorine or bromine atom, by a $C_{1-3}$-alkyl group, by a $C_{1-3}$-alkoxy group or by a trifluoromethyl group, a 2-aminocyclohexyl or 2-aminopyridyl group, optionally with simultaneous decarboxylation.

The reaction is conveniently carried out in a solvent such as methylene chloride, chloroform, carbon tetrachloride, ether, tetrahydrofuran, dioxane, benzene, toluene, acetonitrile or dimethylformamide, optionally in the presence of an acid activating agent or a dehydrating agent, e.g. in the presence of ethyl chloroformate, thionyl chloride, phosphorus trichloride, phosphorus pentoxide, N,N'-dicyclohexylcarbodiimide, N,N'-dicyclohexylcarbodiimide/ N-hydroxysuccinimide, N,N'-carbonyldiimidazole or N,N'-thionyldiimidazole or triphenylphosphine/carbon tetrachloride, or an agent which activates the amino group, e.g. phosphorus trichloride, and optionally in the presence of an inorganic base such as sodium carbonate or a tertiary organic base such as triethylamine or pyridine, which may simultaneously be used as solvents, at temperatures between −25° and 150° C., but preferably at temperatures between −10° C. and the boiling temperature of the solvent used.

An ortho-benzamido compound optionally obtained in this way can then, if necessary, be converted into the desired benzimidazole compound by heating, preferably in a solvent or mixture of solvents such as ethanol, isopropanol, glacial acetic acid, benzene, chlorobenzene, toluene, xylene, glycol, glycolmonomethylether, diethyleneglycol-dimethylether, sulpholane, dimethylformamide or tetraline, optionally in the presence of a condensing agent such as phosphorus oxychloride, thionyl chloride, sulphuryl chloride, sulphuric acid, p-toluenesulphonic acid, methanesulphonic acid, hydrochloric acid, phosphoric acid, polyphosphoric acid, acetic acid anhydride or optionally in the presence of a base such as potassium ethoxide or potassium tert.-butoxide. However, this cyclisation may also be carried out without a solvent and/or condensing agent.

k) In order to prepare compounds of general formula I wherein $R_1$ represents a dihydro-pyridazin-3-one or pyridazin-3-one group which may be substituted in the 2-position by an optionally phenyl-substituted $C_{1-3}$-alkyl group or in the carbon skeleton by one or two $C_{1-3}$-alkyl groups:

Reaction of a carboxylic acid of general formula

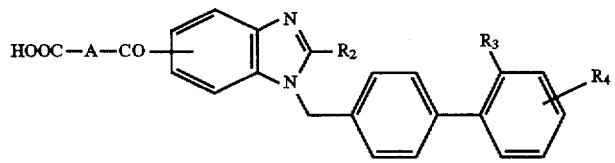

(XIV)

wherein $R_1$ to $R_4$ are defined as hereinbefore and

A represents an ethylene or ethenylene group optionally substituted by one or two $C_{1-3}$-alkyl groups, or the reactive acid derivatives thereof such as the esters, amides or halides thereof, with a hydrazine of general formula $$H_2N-NHR_{12}$$ (XV)

wherein $R_{12}$ represents a hydrogen atom or an optionally phenyl-substituted $C_{1-3}$-alkyl group.

The reaction is conveniently carried out in a solvent such as methanol, ethanol, isopropanol, glacial acetic acid or propionic acid and/or in an excess of the hydrazine or hydrazine hydrate used at temperatures between 0° and 200° C., e.g. at temperatures between 20° and 150° C., but preferably at the boiling temperature of the reaction mixture, and optionally in the presence of an acid such as sulphuric or p-toluenesulphonic acid as condensing agent. The reaction may, however, also be carried out without a solvent.

In the reactions described hereinbefore, any reactive groups present such as hydroxy, amino or alkylamino groups may optionally be protected during the reaction by conventional protecting groups which are split off again after the reaction.

Examples of protecting groups for a hydroxy group are the trimethylsilyl, acetyl, benzoyl, methyl, ethyl, tert.-butyl, benzyl or tetrahydropyranyl groups and protecting groups for an amino, alkylamino or imino group include the acetyl, benzoyl, ethoxycarbonyl and benzyl groups.

The optional subsequent cleaving of a protecting group is preferably carried out by hydrolysis in an aqueous solvent, e.g. in water, isopropanol/water, tetrahydrofuran/water or dioxane/water, in the presence of an acid such as hydrochloric or sulphuric acid or in the presence of an alkali metal base such as sodium hydroxide or potassium hydroxide at temperatures between 0° and 100° C., preferably at the boiling temperature of the reaction mixture. However, a benzyl group is preferably split off by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably 3 to 5 bar.

An isomer mixture of a compound of general formula I thus obtained may if desired be resolved by chromatography using a substrate such as silica gel or aluminium oxide.

Moreover, the compounds of general formula I obtained may be converted into the acid addition salts thereof, more particularly for pharmaceutical use the physiologically acceptable salts thereof with inorganic or organic acids. Suitable acids for this purpose include hydrochloric, hydrobromic, sulphuric, phosphoric, fumaric, succinic, lactic, citric, tartaric or maleic acid.

Furthermore, the new compounds of general formula I thus obtained, if they contain a carboxy or 1H-tetrazolyl group, may if desired subsequently be converted into the salts thereof with inorganic or organic bases, more particularly for pharmaceutical use into the physiologically acceptable salts thereof. Suitable bases include for example sodium hydroxide, potassium hydroxide, cyclohexylamine, ethanolamine, diethanolamine and triethanolamine.

The compounds of general formulae II to XV used as starting materials are known from the literature in some cases or may be obtained by methods known from the literature.

Thus, for example, a compound of general formula II is obtained by alkylation of a corresponding o-amino-nitro compound and subsequent reduction of the nitro group.

A compound of general formula III, V, VI, VII, VIII, IX, X, XII or XIV used as starting material is obtained by alkylation of a corresponding o-phenylenediamine or a corresponding o-amino-nitro compound, followed by reduction of the nitro group and subsequent cyclisation of an o-diamino-phenyl compound thus obtained, optionally followed by the cleaving of any protecting group used or by NH-alkylation of a corresponding 1H-benzimidazole, whilst the isomer mixture thus obtained may subsequently be resolved by conventional methods, e.g. chromatography. Some of the starting compounds mentioned above are described in EP-A-0 392 317.

The new compounds of general formula I and the physiologically acceptable salts thereof have valuable pharmacological properties. They are angiotensin antagonists, particularly angiotensin-II-antagonists.

By way of example, the following compounds

A=4'-[[2-n-propyl-6-(1-methylbenzimidazol-2-yl)-benzimidazol-1-yl]methyl]biphenyl-2-carboxylic acid, B=4'-[[2-n-butyl-6-(3,4,5,6-tetrahydro-phthalimino)-benzimidazol-1-yl]methyl]biphenyl-2-carboxylic acid-dihydrate, C=4'-[[2-n-butyl-6-(2,3-diphenyl-maleic acid imido)-benzimidazol-1-yl]methyl]biphenyl-2-carboxylic acid, D=4'-[[2-n-butyl-6-(2,3-dimethyl-maleic acid imido)-benzimidazol-1-yl]methyl]biphenyl-2-carboxylic acid, E=4'-[[2-n-butyl-6-(N-phenylmethanesulphonylmethylamino)-benzimidazol-1-yl]methyl]biphenyl-2-carboxylic acid, F=4'-[[2-n-butyl-6-(2-oxo-piperidin-1-yl)-benzimidazol-1-yl]methyl]-2-(1H-tetrazol-5-yl)-biphenyl, G=4'-[[2-n-butyl-6-(2-oxo-pyrrolidin-1-yl)-benzimidazol-1-yl]methyl]-2-(1H-tetrazol-5-yl)-biphenyl, H=4'-[[2-n-butyl-6-(2-oxo-hexamethyleneimino)-benzimidazol-1-yl]methyl]-2-(1H-tetrazol-5-yl)-biphenyl, I=4'-[[2-n-butyl-6-(3,3-dimethylglutarimido)-benzimidazol-1-yl]methyl]-2-(1H-tetrazol-5-yl)-biphenyl, J=4'-[[2-n-butyl-6-(N-methylaminocarbonyl-n-pentylamino)-benzimidazol-1-yl]methyl]-2-(1H-tetrazol-5-yl)-biphenyl, K=4'-[[2-n-butyl-6-(cyclohexylaminocarbonyl-n-pentylamino)-benzimidazol-1-yl]methyl]-2-(1H-tetrazol-5-yl)-biphenyl hydrate and L=4'-[[2-n-butyl-6-(2-oxo-3,4-tetramethylenepyrrolidin-1-yl)-benzimidazol-1-yl]methyl]biphenyl-2-carboxylic acid were tested for their biological effects as follows:

Rats (male, 180–220 g) are anaesthetised with sodium hexobarbital (150 mg/kg i.p.). After they have become unconscious, a tracheal cannula is inserted, the animals are pithed and then immediately artificially respirated with a ventilator pump. The arterial blood pressure is recorded by means of a cannula in the carotid artery using a Bell & Howell pressure recorder. The substances are administered in the jugular vein through a cannula.

Test substances are administered in three doses (10, 20 and 30 mg/kg i.v.), with one dose of substance being tested on each animal. Three minutes after the intravenous administration of the test substance, angiotensin-II is administered intravenously in increasing doses and in this way a cumulative dose-activity relationship is achieved for angiotensin-II in the presence of the test substances. The measuring parameter is the increase in arterial blood pressure.

These dose-activity curves are compared with standard curves for angiotensin-II without test substances. Using a computer program, the shift to the right in the dose-activity curves for angiotensin-II as a result of the test substances are determined and corresponding $pA_2$-values are calculated for the test substances.

The $pA_2$ values of the above-mentioned test compounds A to L are between 6.0 and 7.5.

Moreover, when the above-mentioned compounds were administered in a dose of 30 mg/kg i.v. no toxic side effects, e.g. negative inotropic effects or disorders in heart rhythm, were observed. The compounds are therefore well tolerated.

In view of their pharmacological properties, the new compounds and the physiologically acceptable salts thereof are suitable for the treatment of hypertension and cardiac insufficiency and also for treating ischaemic peripheral circulatory disorders, myocardial ischaemia (angina), for the prevention of the progression of cardiac insufficiency after myocardial infarct and for treating diabetic nephropathy, glaucoma, gastrointestinal diseases and bladder diseases.

The new compounds and the physiologically acceptable salts thereof are also suitable for treating pulmonary diseases, e.g. lung oedema and chronic bronchitis, for preventing arterial re-stenosis after angioplasty, for preventing thickening of blood vessel walls after vascular operations, and for preventing arteriosclerosis and diabetic angiopathy. In view of the effects of angiotensin on the release of acetyl choline and dopamine in the brain, the new angiotensin antagonists are also suitable for alleviating central nervous system disorders, e.g. depression, Alzheimer's disease, Parkinson syndrome, bulimia and disorders of cognitive function.

The dosage required to achieve these effects is appropriately, when administered intravenously, 20 to 100 mg, preferably 30 to 70 mg, and, when administered orally, 50 to 200 mg, preferably 75 to 150 mg, 1 to 3 times a day. For this purpose, the compounds of general formula I prepared according to the invention, optionally in conjunction with other active substances such as antihypertensives, diuretics and/or calcium channel blockers, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propylene-glycol, cetyl-stearyl alcohol, carboxymethylcellulose or fatty substances such as hard fat or suitable mixtures thereof, in conventional galenic preparations such as plain or coated tablets, capsules, powders, suspensions or suppositories.

Suitable active ingredients for the above-mentioned combinations are for example atenolol, bendroflumethiazide, chlorothiazide, (di)hydralazine hydrochloride, hydrochlorothiazide, metoprolol, prazosin, propranolol, spironolactone, benzthiazide, cyclothiazide, ethacrinic acid, furosemide, diltiazem, felodipine, nicardipine, nifedipine, nisoldipine and nitrendipine. The individual dosages for these ingredients can be range from about one-fifth of the usually minimal recommended dosage up to the maximum recommended dosage, for example from 15 to 200 mg of hydrochlorothiazide, from 125 to 2000 mg of chlorothiazide, from 15 to 200 mg of ethacrinic acid, from 5 to 80 mg of furosemide, from 20 to 480 mg of propranolol, from 5 to 60 mg of felodipine, from 5 to 60 mg of nifedipine or from 5 to 60 mg of nitrendipine.

The Examples which follow are intended to illustrate the invention:

EXAMPLE 1

4'-[[2-n-propyl-5-(1-methylbenzimidazol-2-yl)-benzimidazol-1-yl]methyl]biphenyl-2-carboxylic acid and 4'-[[2-n-propyl-6-(1-methylbenzimidazol-2-yl)-benzimidazol-1-yl]methyl]biphenyl-2-carboxylic acid a) Methyl-2-n-propyl-benzimidazole-5-carboxylate A solution of 23.9 g (100 mMol) of methyl 3,4-diaminobenzoate dihydrochloride and 11.7 g (110 mMol) of butyric acid chloride in 100 ml of phosphorus oxychloride is refluxed for 2 hours. Then about 80 ml of phosphorus oxychloride are distilled off and the residue is mixed with about 150 ml of water. The oily crude product precipitated is extracted three times with 50 ml of ethyl acetate and after evaporation purified by column chromatography (600 g of silica gel; eluant: methylene chloride/methanol (30:1)).

Yield: 15.0 g of oil (69% of theory)

b) 2-n-Propyl-benzimidazole-5-carboxylic acid-hemisulphate

A solution of 15.0 g (73 mMol) of methyl 2-n-propylbenzimidazole-5-carboxylate and 8 g (200 mMol) of sodium hydroxide in 200 ml of water and 400 ml of ethanol is refluxed for 2 hours. Then the alcohol is distilled off, the aqueous solution is acidified with dilute sulphuric acid (pH 4–5) and evaporated using a rotary evaporator. The product crystallising out is suction filtered, washed with 50 ml of acetone and 50 ml of diethylether and dried.

Yield: 9.1 g (61% of theory),

Melting point: >220° C.

$C_{11}H_{12}N_2O_2 \times 1/2\ H_2SO_4$ (253.26) Calculated: C 52.17 H 5.17 N 11.06 S 6.33 Found: 51.87 5.23 11.11 6.41 c) 2-n-Propyl-5-(1-methylbenzimidazol-2-yl)-benzimidazole

A solution of 6.7 g (25 mMol) of 2-n-propyl-benzimidazole-5-carboxylic acid-hemisulphate and 4.9 g (25 mMol) of 2-methylaminoaniline-dihydrochloride in 200 g of polyphosphoric acid is stirred for 5 hours at 150° C., then poured onto 600 ml of water and made alkaline with concentrated ammonia whilst cooling with ice. The resulting solution is extracted three times with 200 ml of ethyl acetate, the crude product thus obtained is purified by column chromatography (300 g of silica gel; eluant: methylene chloride/methanol=15:1).

Yield: 2.8 g of oil (39% of theory), $C_{18}H_{18}N_4$ (290.37) Calculated: C 74.46 H 6.25 N 9.29 Found: 73.92 6.32 18.96 d) Tert.-butyl 4'-[[2-n-propyl-5-(1-methylbenzimidazol-2-yl)-benzimidazol-1-yl]methyl]biphenyl-2-carboxylic acid and tert.-butyl 4'-[[2-n-propyl-6-(1-methylbenzimidazol-2-yl)-benzimidazol-1-yl]methyl]biphenyl-2-carboxylic acid A solution of 2.0 g (6.9 mMol) of 2-n-propyl-5-(1-methylbenzimidazol-2-yl)-benzimidazole and 0.91 g (7.5 mMol) of potassium tert.-butoxide in 50 ml of dimethylsulphoxide is stirred for 90 minutes at ambient temperature, then 2.6 g (7.5 mMol) of tert.-butyl 4'-bromomethyl-biphenyl-2-carboxylate are added and the mixture is stirred for a further 15 hours at ambient temperature. The mixture is then poured onto 300 ml of water and extracted three times with 50 ml of ethyl acetate. The crude product obtained after evaporation of the organic phase is purified by column chromatography (300 g silica gel; eluant: methylene chloride/methanol=30:1). In this way, 2.7 g (70% of theory) of an isomer mixture are obtained, which when analysed by NMR spectroscopy, contains about 1.18 g of tert.-butyl 4'-[(2-n-propyl-5-(1-methylbenzimidazol-2-yl)-benzimidazol-1-yl)-methyl]biphenyl-2-carboxylate and about 1.52 g of tert.-butyl 4'-[(2-n-propyl-6-(1-methylbenzimidazol-2-yl)-benzimidazol-1-yl)-methyl]biphenyl-2-carboxylate.

$R_f$ value: 0.43 (methylene chloride/methanol=19:1)

e) 4'-[[2-n-Propyl-5-(1-methylbenzimidazol-2-yl)-benzimidazol-1-yl]methyl]biphenyl-2-carboxylic acid and 4'-[[2-n-propyl-6-(1-methylbenzimidazol-2-yl)-benzimidazol-1-yl]methyl]biphenyl-2-carboxylic acid 2.70 g of the isomer mixture obtained in Example 1d are dissolved in 100 ml of methylene chloride, mixed with 40 ml of trifluoroacetic acid and stirred for 4 hours at ambient temperature. The mixture is then evaporated to dryness in vacuo, the residue is dissolved in 100 ml of 2N sodium hydroxide solution, the solution is washed with 50 ml of diethylether and the product mixture is precipitated by acidifying the aqueous phase with acetic acid. By column chromatography (400 g of silica gel, eluant: methylene chloride/methanol=15:1) of the solid thus obtained, 0.7 g (58% of theory) of 4'-[[2-n-propyl-5-(1-methylbenzimidazol-2-yl)-benzimidazol-1-yl]methyl] biphenyl-2-carboxylate are obtained, melting point 219°–220° C.

$C_{32}H_{28}N_4O_2$ (500.60) Calculated: C 76.78 H 5.64 N 11.19 Found: 76.54 5.57 11.01

$R_f$ value: 0.15 (methylene chloride/methanol=9:1) and 0.9 g (74% of theory) of 4'-[[2-n-propyl-6-(1-methylbenzimidazol-2-yl)-benzimidazol-1-yl]methyl] biphenyl-2-carboxylate are obtained, melting point 217°–218° C.

$C_{32}H_{28}N_4O_2$ (500.60) Calculated: C 76.78 H 5.64 N 11.19 Found: 76.63 5.55 11.29

$R_f$ value: 0.40 (methylene chloride/methanol=9:1)

The following compounds are obtained analogously:

4'-[[2-n-propyl-6-(1,6-dimethyl-benzimidazol-2-yl)-benzimidazol-1-yl]methyl]biphenyl-2-carboxylic acid 4'-[[2-n-butyl-6-(1-methyl-5-bromo-benzimidazol-2-yl)-benzimidazol-1-yl]methyl]biphenyl-2-carboxylic acid 4'-[[2-n-butyl-6-(1-methyl-5-methoxy-benzimidazol-2-yl)-benzimidazol-1-yl]methyl]biphenyl-2-carboxylic acid 4'-[[2-n-butyl-6-(1-n-butyl-5-trifluoromethyl-benzimidazol-2-yl)-benzimidazol-1-yl]methyl]biphenyl-2-carboxylic acid 4'-[[2-n-butyl-6-(1-n-hexyl-5-methyl-benzimidazol-2-yl)-benzimidazol-1-yl]methyl]biphenyl-2-carboxylic acid 4'-[[2-n-propyl-6-(1-methyl-5-fluoro-benzimidazol-2-yl)-benzimidazol-1-yl]methyl]biphenyl-2-carboxylic acid 4'-[[2-n-propyl-6-(1-methyl-5-chloro-benzimidazol-2-yl)-benzimidazol-1-yl]methyl]biphenyl-2-carboxylic acid

EXAMPLE 2

4'-[[2-n-Butyl-6-(1-methylbenzimidazol-2-yl)-benzimidazol-1-yl]methyl]biphenyl-2-carboxylic acid Prepared analogously to Example 1 from tert.-butyl 4'-[[2-n-butyl-6-(1-methylbenzimidazol-2-yl)-benzimidazol-1-yl]methyl]biphenyl-2-carboxylate and trifluoroacetic acid in methylene chloride.

Yield: 43% of theory,

Melting point: amorphous $C_{33}H_{30}N_4O_2$ (514.60) Calculated: C 77.02 H 5.88 N 10.89 Found: 76.88 5.83 10.55

$R_f$ value: 0.42 (silica gel; eluant: methylene chloride/ethanol=9:1)

Mass spectrum: $(M+H)^+=515$

EXAMPLE 3

4'-[[6-(Biphenyl-4-carbonylamino)-2-n-butyl-benzimidazol-1-yl]methyl]biphenyl-2-carboxylic acid×0.25 $H_2O$ Prepared analogously to Example 1 from tert.-butyl 4'-[[6-(biphenyl-4-carbonylamino)-2-n-butyl-benzimidazol-1-yl]methyl]biphenyl-2-carboxylate and trifluoroacetic acid in methylene chloride.

Yield: 70.6% of theory,

Melting point: 316°–317° C.

$C_{38}H_{33}N_3O_3 \times 0.25\ H_2O$ (584.20) Calculated: C 78.13 H 5.78 N 7.19 Found: 78.12 5.79 7.08

$R_f$ value: 0.25 (silica gel; eluant: ethyl acetate/ethanol/ammonia=80:40:2)

EXAMPLE 4

4'-[[6-(Biphenylyl-4-aminocarbonylamino)-2-n-butyl-benzimidazol-1-yl]methyl]biphenyl-2-carboxylic acid trifluoroacetate-semihydrate Prepared analogously to Example 1 from tert.-butyl 4'-[[6-(biphenylyl-4-aminocarbonylamino)-2-n-butyl-benzimidazol-1-yl]methyl]biphenyl-2-carboxylate and trifluoroacetic acid in methylene chloride.

Yield: 97.0% of theory,

Melting point: 171°–172° C.

$C_{38}H_{34}N_4O_3 \times CF_3COOH \times 1/2\ H_2O$ (717.74) Calculated: C 66.94 H 5.06 N 7.81 Found: 67.13 4.99 7.76

$R_f$ value: 0.25 (silica gel; eluant: ethyl acetate/ethanol/ammonia=80:40:2)

EXAMPLE 5

4'-[(6-Benzenesulphonamido-2-n-butyl-benzimidazol-1-yl)-methyl]biphenyl-2-carboxylic acid Prepared analogously to Example 1 from tert.-butyl 4'-[(6-benzenesulphonamido-2-n-butyl-benzimidazol-1-yl)-methyl]biphenyl-2-carboxylate and trifluoroacetic acid in methylene chloride.

Yield: 75.0% of theory,

Melting point: 251°–252° C.

$C_{31}H_{29}N_3O_4S$ (539.65) Calculated: C 69.00 H 5.42 N 7.79 S 5.94 Found: 68.96 5.52 7.82 5.86

$R_f$ value: 0.50 (silica gel; eluant: ethyl acetate/ethanol/ammonia=50:45:5)

EXAMPLE 6

4'-[[6-(N-Benzenesulphonyl-methylamino)-2-n-butyl-benzimidazol-1-yl]methyl]biphenyl-2-carboxylic acid Prepared analogously to Example 1 from tert.-butyl 4'-[[6-(N-benzenesulphonyl-methylamino)-2-n-butyl-benzimidazol-1-yl]methyl]biphenyl-2-carboxylate and trifluoroacetic acid in methylene chloride.

Yield: 70.0% of theory,

Melting point: 211°–212° C.

$C_{32}H_{31}N_3O_4S$ (553.68) Calculated: C 69.42 H 5.64 N 7.59 S 5.79 Found: 69.24 5.66 7.53 6.02

$R_f$ value: 0.55 (silica gel; eluant: ethyl acetate/ethanol/ammonia=50:45:5)

EXAMPLE 7

4'-[[2-n-Butyl-6-(cyclohexylmethylaminocarbonylamino)-benzimidazol-1-yl]methyl]biphenyl-2-carboxylic acid-trifluoroacetate Prepared analogously to Example 1 from tert.-butyl 4'-[[2-n-butyl-6-(cyclohexylmethylaminocarbonylamino)-benzimidazol-1-yl]methyl]biphenyl-2-carboxylate and trifluoroacetic acid in methylene chloride.

Yield: 91.1% of theory,

Melting point: 149°–150° C.

$C_{33}H_{38}N_4O_3 \times CF_3COOH$ (652.71) Calculated: C 64.41P H 6.02 N 8.58 Found: 64.23 6.09 8.73

$R_f$ value: 0.25 (silica gel; eluant: ethyl acetate/ethanol/ammonia=80:40:2)

EXAMPLE 8

4'-[[2-n-Butyl-6-(N-cyclohexylmethyl-acetamido)-benzimidazol-1-yl]methyl]biphenyl-2-carboxylic acid Prepared analogously to Example 1 from tert.-butyl 4'-[[2-n-butyl-6-(N-cyclohexylmethyl-acetamido)-benzimidazol-1-yl]methyl]biphenyl-2-carboxylate and trifluoroacetic acid in methylene chloride.

Yield: 78.6% of theory,

Melting point: 185°–187° C.

$C_{24}H_{39}N_3O_3$ (537.70) Calculated: C 75.95 H 7.31 N 7.81 Found: 75.75 7.40 7.65

$R_f$ value: 0.45 (silica gel; eluant: ethyl acetate/ethanol/ammonia=50:45:5)

EXAMPLE 9

4'-[[6-(Bicyclohexyl-4-carbonylamino)-2-n-butyl-benzimidazol-1-yl]methyl]biphenyl-2-carboxylic acid trifluoroacetate Prepared analogously to Example 1 from tert.-butyl 4'-[[6-(bicyclohexyl-4-carbonylamino)-2-n-butyl-benzimidazol-1-yl]methyl]biphenyl-2-carboxylate and trifluoroacetic acid in methylene chloride.

Yield: 93.3% of theory,

Melting point: 104°–106° C.

$C_{38}H_{45}N_3O_3 \times CF_3COOH$ (705.82) Calculated: C 68.07 H 6.57 N 5.95 Found: 68.38 6.64 5.80

$R_f$ value: 0.30 (silica gel; eluant: ethyl acetate/ethanol/ammonia=80:40:2)

EXAMPLE 10

4'-[[6-(Bicyclohexyl-4-aminocarbonylamino)-2-n-butyl-benzimidazol-1-yl]methyl]biphenyl-2-carboxylic acid semitrifluoroacetate-monohydrate Prepared analogously to Example 1 from tert.-butyl 4'-[[6-(bicyclohexyl-4-aminocarbonylamino)-2-n-butyl-benzimidazol-1-yl]methyl]biphenyl-2-carboxylate and trifluoroacetic acid in methylene chloride.

Yield: 94.9% of theory,

Melting point: 119°–120° C.

$C_{38}H_{46}N_4O_3 \times 1/2$ $CF_3$ $COOH \times H_2O$ (681.83) Calculated: C 68.70 H 7.17 N 8.22 Found: 68.32 6.91 7.81

$R_f$ value: 0.30 (silica gel; eluant: ethyl acetate/ethanol/ammonia=80:40:2)

EXAMPLE 11

4'-[[2-n-Butyl-6-(3,4,5,6-tetrahydro-phthalimino)-benzimidazol-1-yl]methyl]biphenyl-2-carboxylic acid dihydrate Prepared analogously to Example 1 from tert.-butyl 4'-[[2-n-butyl-6-(3,4,5,6-tetrahydro-phthalimino)-benzimidazol-1-yl]methyl]biphenyl-2-carboxylate and trifluoroacetic acid in methylene chloride.

Yield: 14.7% of theory,

Melting point: 119°–122° C.

$C_{33}H_{31}N_3O_4 \times 2$ $H_2O$ (533.63) Calculated: C 69.58 H 6.19 N 7.38 Found: 69.77 6.34 7.65

$R_f$ value: 0.45 (silica gel; eluant: ethyl acetate/ethanol/ammonia=80:40:2)

EXAMPLE 12

4'-[[2-n-Butyl-6-(5-dimethylamino-naphthalen-1-sulphonamino)-benzimidazol-1-yl]methyl]biphenyl-2-carboxylic acid-semitrifluoroacetate Prepared analogously to Example 1 from tert.-butyl 4'-[[2-n-butyl-6-(5-dimethylamino-naphthalen-1-sulphonamino)-benzimidazol-1-yl]methyl]biphenyl-2-carboxylate and trifluoroacetic acid in methylene chloride.

Yield: 92.3% of theory,

Melting point: 148°–150° C.

$C_{37}H_{36}N_4O_4S \times 1/2$ $CF_3COOH$ (689.78) Calculated: C 66.17 H 5.33 N 8.12 S 4.64 Found: 65.40 5.33 7.92 5.19

EXAMPLE 13

4'-[[2-n-Butyl-6-(2,3-diphenyl-maleic acid imido)-benzimidazol-1-yl]methyl]biphenyl-2-carboxylic acid Prepared analogously to Example 1 from tert.-butyl 4'-[[2-n-butyl-6-(2,3-diphenyl-maleic acid imido)-benzimidazol-1-yl]methyl]biphenyl-2-carboxylate and trifluoroacetic acid in methylene chloride.

Yield: 82.6% of theory,

Melting point: 236°–237° C.

$C_{41}H_{33}N_3O_4$ (631.73) Calculated: C 77.95 H 5.27 N 6.65 Found: 77.66 5.24 6.56

$R_f$ value: 0.65 (silica gel; eluant: ethyl acetate/ethanol/ammonia=50:45:5)

EXAMPLE 14

4'-[[2-n-Butyl-6-(N-methanesulphonyl-2-phenylethylamino)-benzimidazol-1-yl]methyl]biphenyl-2-carboxylic acid Prepared analogously to Example 1 from tert.-butyl 4'-[[2-n-butyl-6-(N-methanesulphonyl-2-phenylethylamino)-benzimidazol-1-yl]methyl]biphenyl-2-carboxylate and trifluoroacetic acid in methylene chloride.

Yield: 71.4% of theory,

Melting point: 215°–216° C.

$C_{34}H_{35}N_3O_4$ (581.73) Calculated: C 70.20 H 6.06 N 7.22 S 5.51 Found: 69.99 6.14 7.23 5.55

$R_f$ value: 0.25 (silica gel; eluant: ethyl acetate/ethanol/ammonia=80:40:2)

EXAMPLE 15

4'-[[2-n-Butyl-6-(2,3-dimethyl-maleic acid imido)-benzimidazol-1-yl]methyl]biphenyl-2-carboxylic acid Prepared analogously to Example 1 from tert.-butyl 4'-[[2-n-butyl-6-(2,3-dimethyl-maleic acid imido)-benzimidazol-1-yl]methyl]biphenyl-2-carboxylate and trifluoroacetic acid in methylene chloride.

Yield: 69.6% of theory,

Melting point: 289°–290° C.

$C_{31}H_{29}N_3O_4$ (507.59) Calculated: C 73.35 H 5.76 N 8.28 Found: 73.14 5.90 8.20

$R_f$ value: 0.55 (silica gel; eluant: ethyl acetate/ethanol/ammonia=50:45:5)

EXAMPLE 16

4'-[[6-(N-Benzenesulphonyl-n-pentylamino)-2-n-butyl-benzimidazol-1-yl]methyl]biphenyl-2-carboxylic acid Prepared analogously to Example 1 from tert.-butyl 4'-[[6-(N-benzenesulphonyl-n-pentylamino)-2-n-butyl-benzimidazol-1-yl]methyl]biphenyl-2-carboxylate and trifluoroacetic acid in methylene chloride.

Yield: 83.9% of theory,

Melting point: 243°–244° C.

$C_{36}H_{39}N_3O_4S$ (609.78) Calculated: C 70.91 H 6.45 N 6.89 S 5.26 Found: 70.92 6.21 6.98 5.19

$R_f$ value: 0.45 (silica gel; eluant: ethyl acetate/ethanol/ammonia=80:40:2)

EXAMPLE 17

4'-[[2-n-Butyl-6-(N-4-methoxybenzenesulphonyl-n-pentylamino)-benzimidazol-1-yl]methyl]biphenyl-2-carboxylic acid Prepared analogously to Example 1 from tert.-butyl 4'-[[2-n-butyl-6-(N-4-methoxybenzenesulphonyl-n-pentylamino)-benzimidazol-1-yl]methyl]biphenyl-2-carboxylate and trifluoroacetic acid in methylene chloride.

Yield: 84.6% of theory,

Melting point: 207°–208° C.

$C_{37}H_{41}N_3O_5S$ (639.81) Calculated: C 69.46 H 6.46 N 6.57 S 5.01 Found: 69.31 6.50 6.77 5.21

$R_f$ value: 0.50 (silica gel; eluant: ethyl acetate/ethanol/ammonia=80:40:2)

EXAMPLE 18

4'-[[2-n-Butyl-6-(N-4-chlorobenzenesulphonyl-methylamino)-benzimidazol-1-yl]methyl]biphenyl-2-carboxylic acid Prepared analogously to Example 1 from tert.-butyl 4'-[[2-n-butyl-6-(N-4-chlorobenzenesulphonyl-methylamino)-benzimidazol-1-yl]methyl]biphenyl-2-carboxylate and trifluoroacetic acid in methylene chloride.

Yield: 84.8% of theory,
Melting point: 240°–241° C.

$C_{32}H_{30}ClN_3O_4S$ (588.12) Calculated: C 65.35 H 5.14 N 7.14 $C_{16.03}$ S 5.45 Found: 65.02 5.30 7.17 6.21 5.46

EXAMPLE 19

4'-[[2-n-Butyl-6-(N-phenylmethanesulphonyl-methylamino)-benzimidazol-1-yl]methyl]biphenyl-2-carboxylic acid Prepared analogously to Example I from tert.-butyl 4'-[[2-n-butyl-6-(N-phenylmethanesulphonyl-methylamino)-benzimidazol-1-yl]methyl]biphenyl-2-carboxylate and trifluoroacetic acid in methylene chloride.

Yield: 54.9% of theory,
Melting point: 208°–209° C.

$C_{33}H_{33}N_3O_4S$ (567.70) Calculated: C 69.82 H 5.86 N 7.40 S 5.65 Found: 69.54 5.79 7.47 5.59

EXAMPLE 20

4'-[[2-n-Butyl-6-(N-4-methylbenzenesulphonyl-methylamino)-benzimidazol-1-yl]methyl]biphenyl-2-carboxylic acid Prepared analogously to Example 1 from tert.-butyl 4'-[[2-n-butyl-6-(N-4-methylbenzenesulphonyl-methylamino)-benzimidazol-1-yl]methyl]biphenyl-2-carboxylate and trifluoroacetic acid in methylene chloride.

Yield: 92.5% of theory,
Melting point: 259°–260° C.

$C_{33}H_{33}N_3O_4S$ (567.70) Calculated: C 69.82 H 5.86 N 7.40 S 5.65 Found: 69.70 5.90 7.44 5.68

$R_f$ value: 0.25 (silica gel; eluant: ethyl acetate/ethanol/ammonia=80:40:2)

EXAMPLE 21

4'-[[2-n-Butyl-6-(N-n-propylsulphonyl-methylamino)-benzimidazol-1-yl]methyl]biphenyl-2-carboxylic acid Prepared analogously to Example 1 from tert.-butyl 4'-[[2-n-butyl-6-(N-n-propylsulphonyl-methylamino)-benzimidazol-1-yl]methyl]biphenyl-2-carboxylate and trifluoroacetic acid in methylene chloride.

Yield: 67.3% of theory,
Melting point: 222°–223° C.

$C_{29}H_{33}N_3O_4S$ (519.66) Calculated: C 67.03 H 6.40 N 8.09 S 6.17 Found: 67.02 6.49 8.04 6.18

$R_f$ value: 0.20 (silica gel; eluant: ethyl acetate/ethanol/ammonia=80:40:2)

EXAMPLE 22

4'-[[2-n-Butyl-6-(N-4-methoxybenzenesulphonyl-n-propylamino)-benzimidazol-1-yl]methyl]biphenyl-2-carboxylic acid Prepared analogously to Example 1 from tert.-butyl 4'-[[2-n-butyl-6-(N-4-methoxybenzenesulphonyl-n-propylamino)-benzimidazol-1-yl]methyl]biphenyl-2- carboxylate and trifluoroacetic acid in methylene chloride.

Yield: 86.4% of theory,
Melting point: 227°–228° C.

$C_{35}H_{37}N_3O_5S$ (611.75) Calculated: C 68.72 H 6.10 N 6.87 S 5.24 Found: 68.54 6.20 6.88 5.25

$R_f$ value: 0.25 (silica gel; eluant: ethyl acetate/ethanol/ammonia=80:40:2)

EXAMPLE 23

4'-[[2-n-Butyl-6-(N-4-methylbenzenesulphonyl-n-propylamino)-benzimidazol-1-yl]methyl]biphenyl-2-carboxylic acid Prepared analogously to Example 1 from tert.-butyl 4'-[[2-n-butyl-6-(N-4-methylbenzenesulphonyl-n-propylamino)-benzimidazol-1-yl]methyl]biphenyl-2-carboxylic acid and trifluoroacetic acid in methylene chloride.

Yield: 82.8% of theory,
Melting point: 223°–224° C.

$C_{35}H_{37}N_3O_4S$ (595.76) Calculated: C 70.56 H 6.26 N 7.05 S 5.38 Found: 70.25 6.20 7.24 5.61

$R_f$ value: 0.28 (silica gel; eluant: ethyl acetate/ethanol/ammonia=80:40:2)

EXAMPLE 24

4'-[[2-n-Butyl-6-(N-4-chlorobenzenesulphonyl-isopropylamino)-benzimidazol-1-yl]methyl]biphenyl-2-carboxylic acid Prepared analogously to Example 1 from tert.-butyl 4'-[[2-n-butyl-6-(N-4-chlorobenzenesulphonyl-isopropylamino)-benzimidazol-1-yl]methyl]biphenyl-2-carboxylate and trifluoroacetic acid in methylene chloride.

Yield: 82.1% of theory,
Melting point: 260°–261° C.

$C_{34}H_{34}ClN_3O_4S$ (616.17) Calculated: C 66.28 H 5.56 N 6.82 Cl 15.75 S 5.20 Found: 66.05 5.77 7.05 5.87 5.34

$R_f$ value: 0.30 (silica gel; eluant: ethyl acetate/ethanol/ammonia=80:40:2)

EXAMPLE 25

4'-[[6-(N-Benzoyl-isopropylamino)-2-n-butyl-benzimidazol-1-yl]methyl]biphenyl-2-carboxylic acid Prepared analogously to Example 1 from tert.-butyl 4'-[[6-(N-benzoyl-isopropylamino)-2-n-butyl-benzimidazol-1-yl]-methyl]biphenyl-2-carboxylate and trifluoroacetic acid in methylene chloride.

Yield: 58.3% of theory,
Melting point: 209°–210° C.

$C_{35}H_{35}N_3O_3$ (545.68) Calculated: C 77.04 H 6.46 N 7.70 Found: 76.66 6.57 7.65

$R_f$ value: 0.20 (silica gel; eluant: ethyl acetate/ethanol/ammonia=80:40:2)

EXAMPLE 26

4'-[[2-n-Butyl-6-(1H,3H-quinazolin-2,4-dion-3-yl)-benzimidazol-1-yl]methyl]biphenyl-2-carboxylic acid hemihydrate Prepared analogously to Example 1 from tert.-butyl 4'-[[2-n-butyl-6-(1H,3H-quinazolin-2,4-dion-3-yl)-benzimidazol-1-yl]methyl]biphenyl-2-carboxylate and trifluoroacetic acid in methylene chloride.

Yield: 53.1% of theory,
Melting point: 338°–340° C.

$C_{33}H_{28}N_4O_4 \times 1/2\ H_2O$ (553.61) Calculated: C 71.59 H 5.28 N 10.12 Found: 71.19 5.33 10.22

EXAMPLE 27

4'-[[2-n-Butyl-6-(N-4-chlorobenzenesulphonyl-benzylamino)-benzimidazol-1-yl]methyl]biphenyl-2-carboxylic acid Prepared analogously to Example 1 from tert.-butyl 4'-[[2-n-butyl-6-(N-4-chlorobenzenesulphonyl- benzylamino)-benzimidazol-1-yl]methyl]biphenyl-2-carboxylate and trifluoroacetic acid in methylene chloride.

Yield: 64.5% of theory,

Melting point: 212°–213° C.

$C_{38}H_{34}ClN_3O_4S$ (664.22) Calculated: C 68.72 H 5.16 N 6.33 Cl 5.34 S 4.83 Found: 68.76 5.27 6.39 5.62 4.81

$R_f$ value: 0.28 (silica gel; eluant: ethyl acetate/ethanol/ammonia=80:40:2)

EXAMPLE 28

4'-[[2-n-Butyl-6-(N-n-butanesulphonyl-benzylamino)-benzimidazol-1-yl]methyl]biphenyl-2-carboxylic acid Prepared analogously to Example 1 from tert.-butyl 4'-[[2-n-butyl-6-(N-n-butanesulphonyl-benzylamino)-benzimidazol-1-yl]methyl]biphenyl-2-carboxylate and trifluoroacetic acid in methylene chloride.

Yield: 66.4% of theory,

Melting point: 193°–194° C.

$C_{36}H_{39}N_3O_4S$ (609.78) Calculated: C 70.91 H 6.45 N 6.89 S 5.26 Found: 70.76 6.54 6.94 5.40

$R_f$ value: 0.25 (silica gel; eluant: ethyl acetate/ethanol/ammonia=80:40:2)

EXAMPLE 29

4'-[[2-n-Butyl-6-(N-6,7-dimethoxynaphthalen-2-sulphonylmethylamino)-benzimidazol-1-yl]methyl] biphenyl-2-carboxylic acid Prepared analogously to Example 1 from tert.-butyl 4'-[[2-n-butyl-6-(N-6,7-dimethoxynaphthalen-2-sulphonylmethylamino)-benzimidazol-1-yl]methyl] biphenyl-2-carboxylate and trifluoroacetic acid in methylene chloride.

Yield: 87.0% of theory,

Melting point: 261°–262° C.

$C_{38}H_{37}N_3O_6S$ (663.79) Calculated: C 68.76 H 5.62 N 6.33 S 4.83 Found: 69.00 6.00 6.15 5.07

$R_f$ value: 0.23 (silica gel; eluant: ethyl acetate/ethanol/ammonia=80:40:2)

EXAMPLE 30

4'-[[2-n-Butyl-6-(2-oxo-3,4-tetramethylene-pyrrolidin-1-yl)-benzimidazol-1-yl]methyl]biphenyl-2-carboxylic acid Prepared analogously to Example 1 from tert.-butyl 4'-[[2-n-butyl-6-(2-oxo-3,4-tetramethylene-pyrrolidin-1-yl)-benzimidazol-1-yl]methyl]biphenyl-2-carboxylate and trifluoroacetic acid in methylene chloride.

Yield: 38.0% of theory,

Melting point: 146°–148° C.

$C_{33}H_{33}N_3O_3$ (519.65)

$R_f$ value: 0.30 (silica gel; eluant: methylene chloride/ethanol=9:1)

EXAMPLE 31

4'-[[2-n-Butyl-5-(2-oxo-3,4-tetramethylene-pyrrolidin-1-yl)-benzimidazol-1-yl]methyl]biphenyl-2-carboxylic acid Prepared analogously to Example 1 from tert.-butyl 4'-[[2-n-butyl-5-(2-oxo-3,4-tetramethylene-pyrrolidin-1-yl)-benzimidazol-1-yl]methyl]biphenyl-2-carboxylate and trifluoroacetic acid in methylene chloride.

Yield: 15.5% of theory,

Melting point: amorphous $C_{33}H_{33}N_3O_3$ (519.65)

$R_f$ value: 0.20 (silica gel; eluant: methylene chloride/ethanol=9:1)

EXAMPLE 32

4'-[[2-n-Butyl-6-(3,3-dimethylpiperidin-1-yl)-benzimidazol-1-yl]methyl]biphenyl-2-carboxylic acid Prepared analogously to Example 1 from tert.-butyl 4'-[[2-n-butyl-6-(3,3-dimethylpiperidin-1-yl)-benzimidazol-1-yl]methyl]biphenyl-2-carboxylate and trifluoroacetic acid in methylene chloride.

Yield: 86% of theory,

Melting point: from 120° C. (sintering)

$C_{32}H_{37}N_3O_2$ (495.70) Calculated: C 77,54 H 7,52 N 8,48 Found: 77,54 7,24 8,19

$R_f$ value: 0.35 (silica gel; eluant: methylene chloride/ethanol=9:1)

EXAMPLE 33

4'-[[2-n-Butyl-6-heptamethyleneimino-benzimidazol-1-yl]methyl]biphenyl-2-carboxylic acid Prepared analogously to Example 1 from tert.-butyl 4'-[[2-n-butyl-6-heptamethyleneimino-benzimidazol-1-yl]methyl]biphenyl-2-carboxylate and trifluoroacetic acid.

Yield: 71% of theory,

Melting point: 195°–198° C.

$C_{32}H_{37}N_3O_2$ (495.60) Calculated: C 77.55 H 7.52 N 8.48 Found: 74.40 7.66 8.23

$R_f$ value: 0.40 (silica gel; eluant: methylene chloride/ethanol=9:1)

EXAMPLE 34

4'-[[2-n-Butyl-6-(piperidin-1-yl)-benzimidazol-1-yl]methyl]biphenyl-2-carboxylic acid Prepared analogously to Example 1 from tert.-butyl 4'-[[2-n-butyl-6-(piperidin-1-yl)-benzimidazol-1-yl]methyl] biphenyl-2-carboxylate and trifluoroacetic acid.

Yield: 84% of theory,

Melting point: 199°–200° C.

$C_{30}H_{33}N_3O_2$ (467.60) Calculated: C 77.06 H 7.11 N 8.99 Found: 76.85 7.28 9.02

$R_f$ value: 0.40 (silica gel; eluant: methylene chloride/ethanol=9:1)

EXAMPLE 35

4'-[[2-n-Butyl-6-(4-methylpiperidin-1-yl)-benzimidazol-1-yl]methyl]biphenyl-2-carboxylic acid Prepared analogously to Example 1 from tert.-butyl 4'-[[2-n-butyl-6-(4-methyl-piperidin-1-yl)-benzimidazol-1-yl]methyl]biphenyl-2-carboxylate and trifluoroacetic acid.

Yield: 82% of theory,
Melting point: 162°–165° C.

$C_{31}H_{35}N_3O_2$ (481.60) Calculated: C 77.31 H 7.33 N 8.73 Found: 77.20 7.19 8.63

$R_f$ value: 0.40 (silica gel; eluant: methylene chloride/ethanol=9:1)

EXAMPLE 36

4'-[[2-n-Butyl-6-hexamethyleneimino-benzimidazol-1-yl]methyl]biphenyl-2-carboxylic acid Prepared analogously to Example 1 from tert.-butyl 4'-[(2-n-butyl-6-hexamethyleneimino-benzimidazol-1-yl)-methyl]-biphenyl-2-carboxylate and trifluoroacetic acid.

Yield: 34% of theory,
Melting point: 197°–199° C.

$C_{31}H_{35}N_3O_2$ (481.60) Calculated: C 77.31 H 7.33 N 8.73 Found: 76.99 7.35 8.62

$R_f$ value: 0.40 (silica gel; eluant: methylene chloride/ethanol=9:1)

EXAMPLE 37

4'-[[2-n-Propyl-6-(2-oxo-piperidin-1-yl)-benzimidazol-1-yl]methyl]biphenyl-2-carboxylic acid Prepared analogously to Example 1 from tert.-butyl 4'-[[2-n-propyl-6-(2-oxo-piperidin-1-yl)-benzimidazol-1-yl]methyl]biphenyl-2-carboxylate and trifluoroacetic acid.

Yield: 60% of theory,
Melting point: 208°–210° C.

$C_{29}H_{29}N_3O_3$ (467.60) Calculated: C 74.49 H 6.25 N 8.99 Found: 74.00 6.29 8.90

$R_f$ value: 0.50 (silica gel; eluant: methylene chloride/ethanol=9:1)

EXAMPLE 38

4'-[[2-n-Propyl-6-(propanesultam-1-yl)-benzimidazol-1-yl]methyl]biphenyl-2-carboxylic acid Prepared analogously to Example 1 from tert.-butyl 4'-[[2-n-propyl-6-(propanesultam-1-yl)-benzimidazol-1-yl]methyl]biphenyl-2-carboxylate and trifluoroacetic acid.

Yield: 49% of theory,
Melting point: amorphous $C_{28}H_{29}N_3O_4S$ (489.58) Calculated: C 66.23 H 5.56 N 8.56 S 6.55 Found: 66.08 5.50 8.37 6.51

$R_f$ value: 0.47 (silica gel; eluant: methylene chloride/ethanol=9:1)

Mass spectrum: $(M+H)^+=490$

EXAMPLE 39

4'-[[2-n-Propyl-6-(butanesultam-1-yl)-benzimidazol-1-yl]methyl]biphenyl-2-carboxylic acid Prepared analogously to Example 1 from tert.-butyl 4'-[[2-n-propyl-6-(butanesultam-1-yl)-benzimidazol-1-yl]methyl]biphenyl-2-carboxylate and trifluoroacetic acid.

Yield: 57% of theory,
Melting point: amorphous $C_{28}H_{29}N_3O_4S$ (503.63) Calculated: C 66.77 H 5.80 N 8.34 S 6.37 Found: 66.59 5.77 8.18 6.33

$R_f$ value: 0.51 (silica gel; eluant: methylene chloride/ethanol=9:1)

Mass spectrum: $(M+H)^+=504$

EXAMPLE 40

4'-[[2-n-Butyl-6-(butanesultam-1-yl)-benzimidazol-1-yl]methyl]biphenyl-2-carboxylic acid Prepared analogously to Example 1 from tert.-butyl 4'-[[2-n-butyl-6-(butanesultam-1-yl)-benzimidazol-1-yl]methyl]biphenyl-2-carboxylate and trifluoroacetic acid.

Yield: 51% of theory,
Melting point: 203°–205° C.

$C_{29}H_{31}N_3O_4S$ (517.63) Calculated: C 67.29 H 6.04 N 8.12 S 6.19 Found: 67.22 5.97 7.97 6.10

$R_f$ value: 0.52 (silica gel; eluant: methylene chloride/ethanol=9:1)

Mass spectrum: $(M+H)^+=518$

EXAMPLE 41

4'-[[2-n-Butyl-6-(benzoxazol-2-yl)-benzimidazol-1-yl]methyl]-2-(1H-tetrazol-5-yl)-biphenyl a) 2-n-But 1-5-(benzoxazol-2-1-benzimidazole 1.43 g (12 mMol) of thionyl chloride are added dropwise at 10° C. with stirring to a suspension of 2.52 (10 mMol) of 2-n-butyl-benzimidazole-5-carboxylic acid in 15 ml of N-methylpyrrolidinone. The mixture is stirred for a further 15 minutes at ambient temperature, then 1.31 g (11 mMol) of 2-aminophenol are added and the mixture is heated to 140° C. for 2 hours. The mixture is then poured onto about 50 g of ice and 5 ml of 30% sodium hydroxide solution are added with stirring. The crude product precipitated is suction filtered and purified by column chromatography (300 g of silica gel; eluant: methylene chloride+3% ethanol).

Yield: 1.2 g (41% of theory),
Melting point: 118°–120° C.

$C_{18}H_{17}N_3O$ (291.36) Calculated: C 74.20 H 5.88 N 14.42 Found: 73.98 5.97 14.20 b) Isomer mixture of

4'-[[2-n-butyl-6-(benzoxazol-2-yl)-benzimidazol-1-yl]methyl]biphenyl-2-carboxylic acid nitrile and 4'-[[2-n-butyl-5-(benzoxazol-2-yl)-benzimidazol-1-yl]methyl]biphenyl-2-carboxlic acid nitrile A solution of 1 g (3.43 mMol) of 2-n-butyl-5-(benzoxazol-2-yl)-benzimidazole and 0.98 g (3.60 mMol) of 4'-bromomethyl-biphenyl-2-carboxylic acid nitrile in 20 ml dimethylsulphoxide is mixed with 0.41 g (3.6 mMol) of potassium tert.-butoxide and stirred for 48 hours at ambient temperature. The mixture is then poured onto 100 ml of water, saturated with sodium chloride and extracted three times with 30 ml of ethyl acetate. By column chromatography (200 g of silica gel; eluant: ethyl acetate/petroleum ether (1:1)) 1.4 g (85% of theory) of a mixture of the isomers is obtained in the ratio 1:1 and this mixture begins to sinter from 130° C. $C_{32}H_{26}N_4O$ (482.59) Calculated: C 79.64 H 5.43 N 11.61 Found: 79.64 5.36 11.59 c) 4'-[[2-n-Butyl-6-(benzoxazol-2-yl)-benzimidazol-1-yl]methyl]-2-1H-tetrazol-5-1-biphenyl A solution of the (1:1) isomer mixture of 4'-[[2-n-butyl-6-(benzoxazol-2-yl)-benzimidazol-1-yl]methyl]biphenyl-2-carboxylic acid nitrile and 4'-[[2-n-butyl-5-(benzoxazol-2-yl)-benzimidazol-1-yl]methyl]biphenyl-2-carboxylic acid nitrile in 20 ml of dimethylformamide is mixed with 2 g of ammonium chloride and 2 g of sodium azide and heated to 120°–130° C. for 4 hours. After a further 2 g of ammonium chloride and 2 g of sodium azide have been added and the mixture has been heated to 120°–130° C. for a further 18 hours, it is poured onto 100 ml of water. The product mixture precipitated is suction filtered and separated by column chromatography (300 g of silica gel, eluant: methylene chloride+3% ethanol).

Yield: 100 mg (20% of theory) in amorphous form.

$C_{32}H_{27}N_7O$ (525.62) Calculated: C 73.12 H 5.18 N 18.66 Found: 73.10 5.50 18.42

$R_f$ value: 0.75 (silica gel; eluant: methylene chloride/ethanol=9:1)

The following compounds are obtained analogously to Example 41:

4'-[[2-n-butyl-6-(4,5-dihydro-2H-pyridazin-3-on-6-yl)-benzimidazol-1-yl]methyl]-2-(1H-tetrazol-5-yl)-biphenyl 4'-[[2-n-propyl-6-(4,5-dihydro-2H-pyridazin-3-on-6-yl)-benzimidazol-1-yl]methyl]-2-(1H-tetrazol-5-yl)-biphenyl 4'-[[2-ethyl-6-(4,5-dihydro-2H-pyridazin-3-on-6-yl)-benzimidazol-1-yl]methyl]-2-(1H-tetrazol-5-yl)-biphenyl 4'-[[2-n-butyl-6-(2H-pyridazin-3-on-6-yl)-benzimidazol-1-yl]methyl]-2-(1H-tetrazol-5-yl)-biphenyl 4'-[[2-n-propyl-6-(2H-pyridazin-3-on-6-yl)-benzimidazol-1-yl]methyl]-5-(1H-tetrazol-5-yl)-biphenyl 4'-[[2-ethyl-6-(2H-pyridazin-3-on-6-yl)-benzimidazol-1-yl]methyl]-2-(1H-tetrazol-5-yl)-biphenyl 4'-[[2-n-propyl-6-(2-methyl-4,5-dihydro-pyridazin-3-on-6-yl)-benzimidazol-1-yl]methyl]-2-(1H-tetrazol-5-yl)-biphenyl 4'-[[2-n-propyl-6-(2-benzyl-4,5-dihydro-pyridazin-3-on-6-yl)-benzimidazol-1-yl]methyl]-2-(1H-tetrazol-5-yl)-biphenyl 4'-[[2-n-butyl-6-(1-methyl-imidazolin-2-yl)-benzimidazol-1-yl]methyl]-2-(1H-tetrazol-5-yl)-biphenyl 4'-[[2-n-propyl-6-(1-n-hexyl-imidazolin-2-yl)-benzimidazol-1-yl]methyl]-2-(1H-tetrazol-5-yl)-biphenyl 4'-[[2-n-butyl-6-(1-n-butyl-imidazolin-2-yl)-benzimidazol-1-yl]methyl]-2-(1H-tetrazol-5-yl)-biphenyl 4'-[[2-n-propyl-6-(1-cyclopropyl-imidazolin-2-yl)-benzimidazol-1-yl]methyl]-2-(1H-tetrazol-5-yl)-biphenyl 4'-[[2-n-propyl-6-(1-cyclohexyl-imidazolin-2-yl)-benzimidazol-1-yl]methyl]-2-(1H-tetrazol-5-yl)biphenyl 4'-[[2-n-propyl-6-(1-methyl-imidazol-2-yl)-benzimidazol-1-yl]methyl]-2-(1H-tetrazol-5-yl)-biphenyl 4'-[[2-n-butyl-6-(1-methyl-imidazol-2-yl)-benzimidazol-1-yl]methyl]-2-(1H-tetrazol-5-yl)-biphenyl 4'-[[2-n-propyl-6-(1-n-propyl-imidazol-2-yl)-benzimidazol-1-yl]methyl]-2-(1H-tetrazol-5-yl)-biphenyl 4'-[[2-n-propyl-6-(1-n-hexyl-imidazol-2-yl)-benzimidazol-1-yl]methyl]-2-(1H-tetrazol-5-yl)-biphenyl 4'-[[2-n-butyl-6-(1-n-butyl-imidazol-2-yl)-benzimidazol-1-yl]methyl]-2-(1H-tetrazol-5-yl)-biphenyl 4'-[[2-n-propyl-6-(1-cyclopropyl-imidazol-2-yl)-benzimidazol-1-yl]methyl]-2-(1H-tetrazol-5-yl)-biphenyl 4'-[[2-n-propyl-6-(1-cyclohexyl-imidazol-2-yl)-benzimidazol-1-yl]methyl]-2-(1H-tetrazol-5-yl)-biphenyl

EXAMPLE 42

4'-[[2-n-Propyl-5-(1-methylbenzimidazol-2-yl)-benzimidazol-1-yl]methyl]-2-(1H-tetrazol-5-yl)-biphenyl and 4'-[[2-n-propyl-6-(1-methylbenzimidazol-2-yl)-benzimidazol-1-yl]methyl]-2-(1H-tetrazol-5-yl)-biphenyl Prepared analogously to Example 41 from a mixture of 4'-[[2-n-propyl-5-(1-methylbenzimidazol-2-yl)-benzimidazol-1-yl]-methyl]biphenyl-2-carboxylic acid nitrile and 4'-[[2-n-propyl-6-(1-methylbenzimidazol-2-yl)-benzimidazol-1-yl]-methyl]biphenyl-2-carboxylic acid nitrile and sodium azide in dimethylformamide.

5-isomer:

Yield: 29% of theory,

Melting point: amorphous $C_{32}H_{28}N_8$ (524.61) Calculated: C 73.26 H 5.38 N 21.36 Found: 73.03 5.22 21.26

Mass spectrum: $(M+H)^+=525$ 6-isomer:

Yield: 34% of theory,

Melting point: 198°–200° C.

$C_{32}H_{28}N_8$ (524.61) Calculated: C 73.26 H 5.38 N 21.36 Found: 73.11 5.27 21.19

Mass spectrum: $(M+H)^+=525$

EXAMPLE 43

4'-[[2-n-Butyl-6-(1-methylbenzimidazol-2-yl)-benzimidazol-1-yl]methyl]-2-(1H-tetrazol-5-yl)-biphenyl Prepared analogously to Example 41 from 4'-[[2-n-butyl-6-(1-methylbenzimidazol-2-yl)-benzimidazol-1-yl]-methyl] biphenyl-2-carboxylic acid nitrile and sodium azide in dimethylformamide.

Yield: 28% of theory,

Melting point: 224°–226° C.

$C_{33}H_{30}N_8$ (538.63) Calculated: C 73.58 H 5.61 N 20.81 Found: 73.31 5.73 19.99

$R_f$ value: 0.76 (silica gel; eluant: methylene chloride/ethanol=9:1)

Mass spectrum: $(M+H)^+=539$

EXAMPLE 44

4'-[[2-n-Butyl-6-(2-oxo-piperidin-1-yl)-benzimidazol-1-yl]methyl]-2-(1H-tetrazol-5-yl)-biphenyl Prepared analogously to Example 41 from 4'-[[2-n-butyl-6-(2-oxo-piperidin-1-yl)-benzimidazol-1-yl]-methyl] biphenyl-2-carboxylic acid nitrile and sodium azide in dimethylformamide.

Yield: 20% of theory,

Melting point: amorphous $C_{30}H_{31}N_7O$ (505.63) Calculated: C 67.94 H 6.23 N 17.33 Found: 67.67 6.13 17.52

$R_f$ value: 0.30 (silica gel; eluant: methylene chloride/ethanol=9:1)

EXAMPLE 45

4'-[[2-n-Butyl-6-(3,3-dimethylpiperidin-1-yl)-benzimidazol-1-yl]-methyl]-2-(1H-tetrazol-5-yl)-biphenyl Prepared analogously to Example 41 from 4'-[[2-n-butyl-6-(3,3-dimethylpiperidin-1-yl)-benzimidazol-1-yl]-methyl]-2-carboxylic acid nitrile and sodium azide in dimethylformamide.

Yield: 8% of theory,

Melting point: sintering from 148° C.

$C_{32}H_{37}N_7 \times HCl$ (519,70)

Mass spectrum: (M+H)⁺=520

EXAMPLE 46

4'-[[2-n-Butyl-6-(4,4-tetramethyleneglutarimido)-benzimidazol-1-yl]-methyl]-4-chloro-2-(1H-tetrazol-5-yl)-biphenyl Prepared analogously to Example 41 from 4'-[[2-n-butyl-6-(4,4-tetramethyleneglutarimido)-benzimidazol-1-yl]-methyl]-4-chloro-biphenyl-2-carboxylic acid nitrile and sodium azide in dimethylformamide.

Yield: 40% of theory,

Melting point: sintering from 160° C.

$C_{34}H_{34}N_7O_2Cl$ (608.16) Calculated: C 67.15 H 5.64 N 16.12 Found: 66.90 5.86 15.86

$R_f$ value: 0.50 (silica gel; eluant: methylene chloride/ethanol=9:1)

EXAMPLE 47

4'-[[2-n-Butyl-6-(propanesultam-1-yl)-benzimidazol-1yl]-methyl]-2-(1H-tetrazol-5-yl)-biphenyl Prepared analogously to Example 41 from 4'-[[2-n-butyl-6-(propanesultam-1-yl)-benzimidazol-1-yl]-methyl] biphenyl-2-carboxylic acid nitrile and dimethylformamide.

Yield: 46% of theory,

Melting point: 203°–205° C.

$C_{28}H_{29}N_7O_2S$ (527.70) Calculated: C 63.73 H 5.54 N 18.58 S 6.08 Found: 62.52 5.56 18.40 6.00

$R_f$ value: 0.35 (silica gel; eluant: methylene chloride/ethanol=9:1)

EXAMPLE 48

4'-[[2-n-Butyl-6-(butanesultam-1-yl)-benzimidazol-1-yl]-methyl]-2-(1H-tetrazol-5-yl)-biphenyl Prepared analogously to Example 41 from 4'-[[2-n-butyl-6-(butanesultam-1-yl)-benzimidazol-1-yl]-methyl] biphenyl-2-carboxylic acid nitrile and sodium azide in dimethylformamide.

Yield: 30% of theory,

Melting point: 189°–191° C.

$C_{29}H_{31}N_7O_2S$ (541.70) Calculated: C 64.30 H 5.95 N 18.10 S 5.92 Found: 64.40 5.75 17.90 5.85

$R_f$ value: 0.37 (silica gel; eluant: methylene chloride/ethanol=9:1)

EXAMPLE 49

4'-[[2-n-Propyl-6-(butanesultam-1-yl)-benzimidazol-1-yl]-methyl]-2-(1H-tetrazol-5-yl)-biphenyl Prepared analogously to Example 41 from 4'-[[2-n-propyl-6-(butanesultam-1-yl)-benzimidazol-1-yl]-methyl] biphenyl-2-carboxylic acid nitrile and sodium azide in dimethylformamide.

Yield: 37% of theory,

Melting point: 204°–206° C.

$C_{28}H_{29}N_7O_2S$ (527.63) Calculated: C 63.73 H 5.54 N 18.58 S 6.08 Found: 63.70 5.49 18.37 6.19

$R_f$ value: 0.36 (silica gel; eluant: methylene chloride/ethanol=9:1)

Mass spectrum: m/e=527

EXAMPLE 50

Mixture of 4'-[[2-n-butyl-6-(2-hydroxy-cyclohexylaminocarbonyl)-benzimidazol-1-yl]-methyl]-2-(1H-tetrazol-5-yl)-biphenyl and 4'-[[2-n-butyl-5-(2-hydroxy-cyclohexylaminocarbonyl)-benzimidazol-1-yl]-methyl]-2-(1H-tetrazol-5-yl)-biphenyl Prepared analogously to Example 41 from a mixture of 4'-[[2-n-butyl-6-(2-hydroxy-cyclohexylaminocarbonyl)-benzimidazol-1-yl]-methyl]biphenyl-2-carboxylic acid nitrile and 4'-[[2-n-butyl-5-(2-hydroxy-cyclohexylaminocarbonyl)-benzimidazol-1-yl]-methyl]biphenyl-2-carboxylic acid nitrile and sodium azide in dimethylformamide.

Yield: 8% of theory,

Melting point: 198°–200° C.

$C_{32}H_{35}N_7O_2$ (549.70)

$R_f$ value: 0.30 (silica gel; eluant: methylene chloride/ethanol=9:1)

Mass spectrum: (M+H)⁺=550

EXAMPLE 51

4'-[[2-n-Butyl-6-(2-oxo-pyrrolidin-1-yl)-benzimidazol-1-yl]-methyl]-2-(1H-tetrazol-5-yl)-biphenyl Prepared analogously to Example 41 from 4'-[[2-n-butyl-6-(2-oxo-pyrrolidin-1-yl)-benzimidazol-1-yl]methyl]-biphenyl-2-carboxylic acid nitrile and sodium azide in dimethylformamide.

Yield: 15% of theory,

Melting point: 153°–155° C.

$C_{29}H_{29}N_7O$ (491.60) Calculated: C 70.85 H 5.95 N 19.95 Found: 70.79 6.17 19.71

$R_f$ value: 0.45 (silica gel; eluant: methylene chloride/ethanol=9:1)

Mass spectrum: (M+H)⁺=492

EXAMPLE 52

Mixture of 4'-[[2-n-butyl-6-(1,1-dimethyl-2-hydroxy-ethylamino-carbonyl)-benzimidazol-1-yl]-methyl]-2-(1H-tetrazol-5-yl)-biphenyl and 4'-[[2-n-butyl-5-(1,1-dimethyl-2-hydroxy-ethylamino-carbonyl)-benzimidazol-1-yl]-methyl]-2-(1H-tetrazol-5-yl)-biphenyl Prepared analogously to Example 41 from a mixture of 4'-[[2-n-butyl-6-(1,1-dimethyl-2-hydroxy-ethylamino-carbonyl)-benzimidazol-1-yl]-methyl]biphenyl-2-carboxylic acid nitrile and 4'-[[2-n-butyl-5-(1,1-dimethyl-2-hydroxy-ethylamino-carbonyl)-benzimidazol-1-yl]-methyl] biphenyl-2-carboxylic acid nitrile and sodium azide in dimethylformamide.

Yield: 14% of theory,

Melting point: amorphous $C_{30}H_{33}N_7O_2$ (523.60)

$R_f$ value: 0.30 (silica gel; eluant: methylene chloride/ethanol=9:1)

Mass spectrum: (M+H)⁺=524

EXAMPLE 53

4'-[[2-n-Butyl-6-(2-oxo-hexamethyleneimino)-benzimidazol-1-yl]-methyl]-2-(1H-tetrazol-5-yl)-biphenyl Prepared analogously to Example 41 from 4'-[[2-n-butyl-6-(2-oxo-hexamethyleneimino)-benzimidazol-1-yl]-methyl]

biphenyl-2-carboxylic acid nitrile and sodium azide in dimethylformamide.

Yield: 34% of theory,

Melting point: amorphous $C_{31}H_{33}N_7O$ (519.70) Calculated: C 71.65 H 6.40 N 18.87 Found: 70.99 6.32 18.75

$R_f$ value: 0.15 (silica gel; eluant: methylene chloride/ethanol=9:1)

EXAMPLE 54

4'-[[2-n-Propyl-6-(2-oxo-piperidin-1-yl)-benzimidazol-1-yl]-methyl]-2-(1H-tetrazol-5-yl)-biphenyl Prepared analogously to Example 41 from 4'-[[2-n-propyl-6-(2-oxo-piperidin-1-yl)-benzimidazol-1-yl]-methyl]biphenyl-2-carboxylic acid nitrile and sodium azide in dimethylformamide.

Yield: 14.5% of theory,

Melting point: sintering from 125° C.

$C_{29}H_{29}N_7O$ (491.60)

$R_f$ value: 0.25 (silica gel; eluant: methylene chloride/ethanol=9:1)

Mass spectrum: $(M+H)^+=492$

EXAMPLE 55

4'-[[2-n-Butyl-6-(3,3-dimethylglutarimido)-benzimidazol-1-yl]methyl]-2-(1H-tetrazol-5-yl)-biphenyl a) 4'[[2-n-Butyl-6-(3,3-dimethylglutarimido)-benzimidazol-1-yl]methyl]-2-(1-triphenylmethyl-tetrazol-5-yl)-biphenyl 1.8 g (3.3 mMol) of 4'-bromomethyl-2-(1-triphenylmethyl-tetrazol-5-yl)-biphenyl are added to a solution of 1.04 g (3.3 mMol) of 2-n-butyl-5-(3,3-dimethylglutarimido)-benzimidazole and 425 mg (3.8 mMol) of potassium tert.-butoxide in 25 ml of dimethylsulphoxide. The mixture is stirred for 3 hours at ambient temperature, then stirred into 150 ml of water, extracted three times with 30 ml of ethyl acetate, then the organic extracts are dried and concentrated by evaporation. The residue obtained is purified by column chromatography (300 g of silica gel; eluant: ethyl acetate/petroleum ether (2:1)).

Yield: 400 mg (15% of theory), $R_f$ value: 0.38 (ethyl acetate/petroleum ether=6:1)

b) 4'-[[2-n-Butyl-6-(3,3-dimethylglutarimido)-benzimidazol-1-yl]methyl]-2-(1H-tetrazol-5-yl)-biphenyl A solution of 400 mg (0.5 mMol) of 4'-[[2-n-butyl-6-(3,3-dimethylglutarimido)-benzimidazol-1-yl]-methyl]-2-(1-triphenylmethyl-tetrazol-5-yl)-biphenyl in 10 ml of methanol is mixed with 1.5 ml of methanolic hydrochloric acid and stirred for 2 hours at ambient temperature, then concentrated by evaporation, the residue is mixed with 15 ml of water and made alkaline with concentrated ammonia, whereupon the product goes into solution. By acidification with glacial acetic acid, the crude product is precipitated and then purified by column chromatography (150 g of silica gel; eluant: methylene chloride +5% ethanol).

Yield: 150 mg (55% of theory),

Melting point: 184°–186° C.

$C_{32}H_{33}N_7O_2$ (547.70) Calculated: C 70.18 H 6.07 N 17.90 Found: 69.98 6.20 17.67

EXAMPLE 56

4'-[[2-n-Butyl-6-(N-methylaminocarbonyl-n-pentylamino)-benzimidazol-1-yl]methyl]-2-(1H-tetrazol-5-yl)-biphenyl Prepared analogously to Example 55 from 4'-[[2-n-butyl-6-(N-methylaminocarbonyl-n-pentylamino)-benzimidazol-1-yl]methyl]-2-(1-triphenylmethyl-tetrazol-5-yl)-biphenyl and hydrochloric acid in ethanol.

Yield: 53.8% of theory,

Melting point: 124°–126° C.

$C_{33}H_{38}N_8O$ (550.71)

$R_f$ value: 0.25 (silica gel; eluant: methylene chloride/ethanol=9:1) Calculated: C 69.79 H 6.95 N 20.35 Found: 69.78 7.05 20.31

Mass spectrum: $(M+H)^+=492$

EXAMPLE 57

4'-[[2-n-Butyl-5-(N-methylaminocarbonyl-n-pentylamino)-benzimidazol-1-yl]methyl]-2-(1H-tetrazol-5-yl)-biphenyl-dihydrate Prepared analogously to Example 55 from 4'-[[2-n-butyl-5-(N-methylaminocarbonyl-n-pentylamino)-benzimidazol-1-yl]methyl]-2-(1-triphenylmethyl-tetrazol-5-yl)-biphenyl and hydrochloric acid in ethanol.

Yield: 76.2% of theory,

Melting point: 201°–203° C.

$C_{32}H_{38}N_8O \times 2\ H_2O$ (586.74) Calculated: C 65.50 H 7.21 N 19.09 Found: 65.43 7.07 19.12

EXAMPLE 58

4'-[[2-n-Butyl-6-(N-cyclohexylaminocarbonyl-n-pentylamino)-benzimidazol-1-yl]methyl]-2-(1H-tetrazol-5-yl)-biphenyl-hydrate Prepared analogously to Example 55 from 4'-[[2-n-butyl-6-(N-cyclohexylaminocarbonyl-n-pentylamino)-benzimidazol-1-yl]methyl]-2-(1-triphenylmethyl-tetrazol-5-yl)-biphenyl and hydrochloric acid in ethanol.

Yield: 95.2% of theory,

Melting point: 128°–132° C.

$C_{37}H_{46}N_8O \times H_2O$ (636.84) Calculated: C 69.78 H 7.59 N 17.59 Found: 69.61 7.71 17.41

$R_f$ value: 0.45 (silica gel; eluant: ethanol/ammonia=80/40/2)

EXAMPLE 59

4'-[[2-n-Butyl-5-(N-cyclohexylaminocarbonyl-n-pentylamino)-benzimidazol-1-yl]methyl]-2-(1H-tetrazol-5-yl)-biphenyl-hydrate Prepared analogously to Example 55 from 4'-[[2-n-butyl-5-(N-cyclohexylaminocarbonyl-n-pentylamino)-benzimidazol-1-yl]methyl]-2-(1-triphenylmethyl-tetrazol-5-yl)-biphenyl and hydrochloric acid in ethanol.

Yield: 88.6% of theory,

Melting point: 117°–120° C.

$C_{37}H_{46}N_8O \times H_2O$ (636.84) Calculated: C 69.78 H 7.59 N 17.59 Found: 70.06 7.58 17.56

$R_f$ value: 0.45 (silica gel; eluant: ethanol/ammonia=80/40/2)

EXAMPLE 60

4'-[[2-n-Butyl-6-(5-dimethylaminonaphthalen-1-sulphonamino)-benzimidazol-1-yl]methyl]-2-(1H-tetrazol-5-yl)-biphenyl-hydrate Prepared analogously to Example 55 from 4'-[[2-n-butyl-6-(5-dimethylaminonaphthalen-1-sulphonamino)- benzimidazol-1-yl]methyl]-2-(1-triphenylmethyl-tetrazol-5-yl)-biphenyl and hydrochloric acid in ethanol.

Yield: 44.7% of theory, $C_{37}H_{36}N_8O_2S \times H_2O$ (674.81) Calculated: C 65.85 H 5.67 N 16.60 S 4.75 Found: 65.80 5.46 16.42 4.90

EXAMPLE 61

4'-[[2-n-Butyl-6-(2-oxo-3,4-tetramethylene-pyrrolidin-1-yl)-benzimidazol-1-yl]methyl]biphenyl-2-carboxylic acid 420 mg (0.81 mMol) of 4'-[[2-n-butyl-6-(2-oxo-1,2-dihydro-3,4-tetramethylene-pyrrol-1-yl)-benzimidazol-1-yl]methyl]biphenyl-2-carboxylic acid are dissolved in 60 ml of methanol and 60 ml of ethyl acetate and hydrogenated with the addition of 200 mg of palladium on charcoal (10%) under 5 bar of hydrogen pressure and at 40° C. The catalyst is removed by suction filtering, the solvent is evaporated off and the crude product is purified by column chromatography (200 g of silica gel; eluant: methylene chloride +3% ethanol).

Yield: 260 mg (62% of theory),

Melting point: amorphous $C_{33}H_{35}N_3O_3$ (521.67) Calculated: C 75.98 H 6.76 N 8.06 Found: 75.75 6.62 8.24

EXAMPLE 62

Mixture of 4'-[[2-n-butyl-6-(5,5-pentamethylene-oxazolin-2-yl)-benzimidazol-1-yl)-methyl]-2-(1H-tetrazol-5-yl)-biphenyl and 4'-[[2-n-butyl-5-(5,5-pentamethylene-oxazolin-2-yl)-benzimidazol-1-yl)-methyl]-2-(1H-tetrazol-5-yl)-biphenyl A solution of 930 mg (2 mMol) of an isomer mixture of 4'-[[2-n-butyl-6-carboxy-benzimidazol-1-yl]-methyl]-2-(1H-tetrazol-5-yl)-biphenyl and 4'-[[2-n-butyl-5-carboxy-benzimidazol-1-yl]-methyl]-2-(1H-tetrazol-5-yl)-biphenyl and 356 mg (2.2 mMol) of carbonyldiimidazole in 30 ml of tetrahydrofuran is stirred for 30 minutes at ambient temperature. Then 332 mg (2 mMol) of 1-(aminomethyl)-cyclohexanol-dihydrochloride are added and the mixture is stirred for a further 15 hours at ambient temperature. The mixture is then concentrated by evaporation, 2 ml of thionyl chloride are slowly added dropwise, the mixture is stirred for one hour, the thionyl chloride is distilled off and the residue is mixed with 5 ml of ice water. The insoluble crude product is purified by column chromatography (150 g of silica gel; eluant: methylene chloride +5% ethanol). In this way, 25 mg (2% of theory) of a mixture of 4'-[[2-n-butyl-6-(5,5-pentamethylene-oxazolin-2-yl)-benzimidazol-1-yl]-methyl]-2-(1H-tetrazol-5-yl)-biphenyl and 4'-[[2-n-butyl-5-(5,5-pentamethylene-oxazolin-2-yl)-benzimidazol-1-yl]-methyl]-2-(1H-tetrazol-5-yl)-biphenyl is obtained.

Melting point: from 215° C. (decomp.)

$C_{33}H_{35}N_7O$ (545.67)

Mass spectrum: $(M+H)^+=546$

EXAMPLE 63

4'-[[2-n-Butyl-6-(N-methyl-phenylaminocarbonylamino)-benzimidazol-1-yl]-methyl]biphenyl-2-carboxylic acid A solution of 0.8 g (2.00 mMol) of 4'-[[2-n-butyl-6-aminobenzimidazol-1-yl]-methyl]biphenyl-2-carboxylic acid and 0.9 g of N-methyl-isatoic acid anhydride in 3 ml of pyridine is refluxed for 48 hours, then evaporated to dryness, the residue is suspended in about 5 ml of methylene chloride, suction filtered, washed with a further 5 ml of methylene chloride and dried.

Yield: 0.66 g (62% of theory),

Melting point: 274°–276° C.

$C_{33}H_{32}N_4O_3$ (532.60) Calculated: C 74.41 H 6.06 N 10.57 Found: 74.23 5.94 10.66

EXAMPLE 64

4'-[[2-n-Butyl-5-(3-carboxy-propionyl)-benzimidazol-1-yl]-methyl]biphenyl-2-carboxylic acid A solution of 200 mg (0.39 mMol) of methyl 4'-[[2-n-butyl-5-(3-methoxycarbonyl-propionyl)-benzimidazol-1-yl]-methyl]biphenyl-2-carboxylate and 0.75 ml of sodium hydroxide solution in 4 ml of ethanol is stirred for 2 hours at 75° C., then mixed with 40 ml of water and acidified with glacial acetic acid. The alcohol is then distilled off, the resulting mixture is stirred for one hour at ambient temperature, the product precipitated is suction filtered, washed with 10 ml of water and dried.

Yield: 120 mg (64% of theory),

Melting point: 200°–202° C.

$C_{29}H_{28}N_2O_4$ (484.60) Calculated: C 71.88 H 5.83 N 5.78 Found: 71.66 5.86 5.63

EXAMPLE 65

4'-[[2-n-Butyl-6-(3-carboxy-2-methyl-propionyl)-benzimidazol-1-yl]methyl]biphenyl-2-carboxylic acid×0.25 $H_2O$ Prepared analogously to Example 64 from methyl 4'-[[2-n-butyl-6-(3-methoxycarbonyl-2-methyl-propionyl)-benzimidazol-1-yl]methyl]biphenyl-2-carboxylate and sodium hydroxide solution in ethanol.

Yield: 18% of theory,

Melting point: 193°–194° C.

$C_{30}H_{30}N_2O_5 \times 1/4 \ H_2O$ (498.60) Calculated: C 71.62 H 6.11 N 5.56 Found: 71.72 6.09 5.68

$R_f$ value: 0.37 (silica gel; eluant: methylene chloride/ethanol/glacial acetic acid=18/1/0.05)

EXAMPLE 66

4'-[[2-n-Butyl-6-(3-carboxy-propionyl)-benzimidazol-1-yl]methyl]biphenyl-2-carboxylic acid Prepared analogously to Example 64 from methyl 4'-[[2-n-butyl-6-(3-methoxycarbonyl-propionyl)-benzimidazol-1-yl]methyl]biphenyl-2-carboxylate and sodium hydroxide solution in ethanol.

Yield: 97% of theory,

Melting point: 240°–242° C.

$C_{29}H_{28}N_2O_5$ (484.60) Calculated: C 71.88 H 5.83 N 5.78 Found: 71.74 6.07 5.93

EXAMPLE 67

4'-[[2-n-Butyl-6-(2,3-dimethylmaleic acid imino)-benzimidazol-1-yl]methyl]biphenyl-2-carboxylic acid 52.5 mg (0.1 mMol) of 4'-[[2-n-butyl-6-(2,3-dimethylmaleic acid amino)-benzimidazol-1-yl]-methyl]- biphenyl-2-carboxylate are heated to boiling for one hour in 2 ml of bis-(2-methoxy-ethyl)-ether. The solvent is removed by distillation and the oily residue is distributed in ethyl acetate/water. The organic phase is washed twice more with water, dried with magnesium sulphate and concentrated by rotary evaporation. The residue is triturated in 1 ml of acetone, suction filtered, washed with ether and dried in vacuo at 75° C.

Yield: 29.0 mg (57.2% of theory),

Melting point: 289°–291° C.

$C_{31}H_{29}N_3O_4$ (507.59) Calculated: C 73.35 H 5.76 N 8.29 Found: 73.50 5.64 8.10

EXAMPLE 68

4'-[[2-n-Butyl-6-(3,4,5,6-tetrahydro-phthalimino)-benzimidazol-1-yl]methyl]biphenyl-2-carboxylic acid-hydrate 0.275 g (0.5 mMol) of 4'-[[2-n-butyl-6-(2-carboxy-3,4,5,6-tetrahydrobenzamino)-benzimidazol-1-yl]-methyl]biphenyl-2-carboxylate are refluxed for 4 hours in 5 ml of pyridine. The mixture is evaporated to dryness in vacuo by rotary evaporation and the crude product is recrystallised from acetone. It is suction filtered, washed with acetone and dried in vacuo at 70° C.

Yield: 0.2 g (72.4% of theory),

Melting point: 226°–228° C.

$C_{30}H_{31}H_3O_4 \times H_2O$ (551.64) Calculated: C 71.85 H 6.03 N 7.62 Found: 71.83 5.90 7.61

EXAMPLE 69

Tert.-butyl 4'-[[2-n-butyl-6-(pyrrolidinocarbonylamino)-benzimidazol-1-yl]methyl]biphenyl-2-carboxylate 2.0 g (15 mMol) of pyrrolidinocarbonyl chloride are placed in 50 ml of dry chloroform and 2.3 g (6 mMol) of tert.-butyl 4'-[(6-amino-2-n-butyl-benzimidazol-1-yl)-methyl]biphenyl-2-carboxylate dissolved in 50 ml of dry pyridine are added dropwise for one hour. The reaction solution is stirred for a further 24 hours and then concentrated by rotary evaporation. The oily residue is distributed in ethyl acetate and 10% sodium hydrogen carbonate solution, the organic phase is separated off and, after drying with magnesium sulphate, concentrated by rotary evaporation. Purification is carried out using a silica gel column (particle size: 0.063–0.2 mm), eluting with petroleum ether/ethyl acetate=3:7. The corresponding column fractions are concentrated by rotary evaporation and dried in vacuo at 50° C.

Yield: 1.7 g (61.8% of theory),

Melting point: 68°–70° C. (amorphous)

$C_{34}H_{40}N_4O_3$ (552.72)

$R_f$ value: 0.35 (silica gel; eluant: ethyl acetate/ethanol= 19:1)

EXAMPLE 70

4'-[[2-n-Butyl-6-(pyrrolidinocarbonylamino)-benzimidazol-1-yl]methyl]biphenyl-2-carboxylic acid trifluoroacetate-monohydrate Prepared analogously to Example 1 from tert.-butyl 4'-[[2-n-butyl-6-(pyrrolidinocarbonylamino)-benzimidazol-1-yl]methyl]biphenyl-2-carboxylate and trifluoroacetic acid/methylene chloride.

Yield: 91.7% of theory,

Melting point: 233°–234° C.

$C_{30}H_{32}N_4O_3 \times CF_3COOH \times H_2O$ (628.25) Calculated: C 61.14 H 5.61 N 8.91 Found: 61.25 5.62 9.09

$R_f$ value: 0.48 (silica gel; eluant: ethyl acetate/ethanol/ammonia=50:45:5)

EXAMPLE 71

4'-[[2-n-Butyl-6-(2,3-dimethylmaleic acid imino)-benzimidazol-1-yl]methyl]biphenyl-2-carboxylic acid 314 mg (0.5 mMol) of 4'-[(6-amino-2-n-butyl-benzimidazol-1-yl)-methyl]biphenyl-2-carboxylic acid trifluoroacetate are refluxed together with 76 mg (0.6 mMol) of 2,3-dimethylmaleic acid anhydride in 10 ml of pyridine for 18 hours. The solvent is then removed by rotary evaporation and the oily substance is distributed in ethyl acetate and 10% sodium hydrogen carbonate solution. The organic phase is separated off, dried with magnesium sulphate and concentrated by rotary evaporation after being filtered. By trituration with acetone and ether, a white crystalline product is obtained which is dried at 50° C. in vacuo after suction filtering.

Yield: 165 mg (65.0% of theory),

Melting point: 288°–290° C.

$C_{31}H_{29}N_3O_4$ (507.59) Calculated: C 73.35 H 5.76 N 8.29 Found: 73.14 5.94 8.32

EXAMPLE 72

4'-[(2-n-Butyl-6-hexahydrohomophthalimino-benzimidazol-1yl)-methyl]biphenyl-2-carboxylic acid Prepared analogously to Example 71 from 4'-[(6-amino-2-n-butyl-benzimidazol-1-yl)-methyl]biphenyl-2-carboxylic acid and hexahydrohomophthalic acid anhydride in pyridine.

Yield: 15.3% of theory,

Melting point: 183°–185° C.

$C_{34}H_{35}N_3O_4$ (549.67) Calculated: C 74.29 H 6.49 N 7.64 Found: 74.09 6.47 7.80

EXAMPLE 73

4'-[[2-n-Butyl-6-(benzofuran-2-carbonylamino)-benzimidazol-1-yl]methyl]biphenyl-2-carboxylic acid Prepared analogously to Example 71 from 4'-[(6-amino-2-n-butyl-benzimidazol-1-yl)-methyl]biphenyl-2-carboxylic acid and benzofuran-2-carboxylic acid anhydride in pyridine.

Yield: 80.7% of theory,

Melting point: 321°–323° C.

$C_{34}H_{39}N_3O_4$ (543.62) Calculated: C 75.12 H 5.38 N 7.73 Found: 74.92 5.45 7.87

EXAMPLE 74

4'-[[2-n-Butyl-6-(3-benzyl-3,4,5,6-tetrahydro-2(1H)-pyrimidinon-1-yl)-benzimidazol-1-yl]methyl]biphenyl-2-carboxylic acid Prepared analogously to Example 1 from tert.-butyl 4'-[[2-n-butyl-6-(3-benzyl-3,4,5,6-tetrahydro-2(1H)-pyrimidinon-1-yl)-benzimidazol-1-yl]-methyl]biphenyl-2-carboxylate and trifluoroacetic acid in methylene chloride.

Yield: 42.2% of theory,

Melting point: 119°–122° C.

$C_{36}H_{36}N_4O_3 \times H_2O$ (590.72) Calculated: C 73.20 H 6.48 N 9.48 Found: 73.11 6.50 9.67

EXAMPLE 75

4'-[[2-n-Butyl-6-(2-carboxy-cyclohexylmethylcarbonylamino)-benzimidazol-1-yl]methyl]biphenyl-2-carboxylic acid hydrate a) Tert.-butyl 4'-[[2-n-butyl-6-(2-carboxy-cyclohexylmethylcarbonylamino)-benzimidazol-1-yl]-methyl]biphenyl-2-carboxylate 1.3 g (2.86 mMol) of tert.-butyl 4'-[(6-amino-2-n-butyl-benzimidazol-1-yl)-methyl]biphenyl-2-carboxylate, 0.6 g (5.35 mMol) of hexahydrohomophthalic acid anhydride and 5 ml of pyridine are refluxed with stirring for 3 hours. Then the pyridine is removed by rotary evaporation in vacuo, the residue is crystallised from acetone, washed with acetone and dried in vacuo at 70° C.

Yield: 0.67 g (37.6% of theory),

Melting point: 227°–229° C.

$C_{38}H_{45}N_3O_5$ (623.79) Calculated: C 73.17 H 7.27 N 6.74 Found: 72.93 7.15 6.94 b) 4'-[[2-n-butyl-6-(2-carboxy-cyclohexylmethylcarbonylamino)-benzimidazol-1-yl]methyl]biphenyl-2-carboxylic acid 0.6 g (0.06 mMol) of tert.-butyl 4'-[[2-n-butyl-6-(2-carboxy-cyclohexylmethylcarbonylamino)-benzimidazol-1-yl]methyl]biphenyl-2-carboxylate, 30 ml of methylene chloride and 10 ml of trifluoroacetic acid are stirred for 3 hours at ambient temperature. The mixture is diluted with 20 ml of methylene chloride, extracted with water, the organic phase is dried over sodium sulphate and evaporated to dryness. The residue is dissolved in ethanol and made alkaline by the addition of ammonia. The solvent is distilled off in vacuo. The remaining aqueous solution is acidified with acetic acid, the product which crystallises out is suction filtered, washed with water and dried in vacuo at 70° C.

Yield: 0.55 g (98.2% of theory),

Melting point: 160°–162° C.

$C_{34}H_{37}N_3O_5 \times H_2O$ (585.68) Calculated: C 69.72 H 6.71 N 7.17 Found: 69.63 6.64 7.33

EXAMPLE 76

4'-[[2-n-Butyl-6-(2-carboxy-3,4,5,6-tetrahydrobenzamino)-benzimidazol-1-yl]methyl]biphenyl-2-carboxylic acid 0.4 g (1 mMol) of 4'-[(6-amino-2-n-butyl-benzimidazol-1-yl)-methyl]biphenyl-2-carboxylic acid, dissolved in 7 ml of pyridine, are mixed with 0.34 g (1.1 mMol) of 1-cyclohexene-1,2-dicarboxylic acid anhydride at ambient temperature and stirred for 2½ hours. The mixture is cooled with ice and the product which crystallises out is suction filtered, washed with cooled acetone and dried in vacuo at 70° C.

Yield: 0.37 g (67.2% of theory),

Melting point: 250°–252° C.

$C_{33}H_{33}N_3O_5$ (551.64) Calculated: C 71.85 H 6.03 N 7.62 Found: 71.70 5.99 7.60

EXAMPLE 77

4'-[[2-n-Propyl-6-(1-methylbenzimidazol-2-yl)-benzimidazol-1-yl]methyl]biphenyl-2-carboxylic acid 604 mg (1.0 mMol) of tert.-butyl 4'-[[2-nitro-5-(1-methylbenzimidazol-2-yl)-N-n-butyryl-anilino]methyl] biphenyl-2-carboxylate are stirred in 50 ml of methylene chloride with the addition of 10 ml of trifluoroacetic acid at ambient temperature for 3 hours. The solvent is then distilled off, the residue is dissolved in 25 ml of glacial acetic acid and hydrogenated at 80° C. with the addition of 500 mg of 10% palladium/charcoal. In order to work up the product, the solvent is distilled off in vacuo, the residue is dissolved in 30 ml of 2N sodium hydroxide solution and the solution is washed with 20 ml of diethyl ether. The crude product precipitated by the acidification of the aqueous phase is purified by subsequent column chromatography (80 g silica gel, eluant: methylene chloride/methanol=15:1).

Yield: 90 mg (18% of theory),

Melting point: 214°–216° C.

$C_{32}H_{28}N_4O_2$ (500.60) Calculated: C 76.78 H 5.64 N 11.19 Found: 76.58 5.49 11.30

EXAMPLE 78

4'-[[2-n-Propyl-6-(1-methylbenzimidazol-2-yl)-benzimidazol-1-yl]methyl]biphenyl-2-carboxylic acid A suspension of 940 mg (2.0 mMol) of tert.-butyl 4'-[(2-n-propyl-6-carboxy-benzimidazol-1-yl)-methyl]biphenyl-2-carboxylate and 320 mg (2.0 mMol) of carbonyldiimidazole in a solution of 1.0 ml of triethylamine in 30 ml of tetrahydrofuran is stirred for 30 minutes at ambient temperature, then 250 mg (2.0 mMol) of 2-methylaminoaniline are added and the mixture is stirred for a further 16 hours. It is then evaporated to dryness and the residue is refluxed in 20 ml of phosphorus oxychloride, with stirring, for 1 hour. The majority of the phosphorus oxychloride is then distilled off, the dark, greasy residue is decomposed with 30 ml of water, the strongly acidic suspension thus obtained is refluxed for about 1 hour, adjusted to pH 6 after cooling and then concentrated by evaporation. The crude product obtained is purified by column chromatography (120 g of silica gel, eluant: methylene chloride/methanol=15:1).

Yield: 73 mg (7.3% of theory),

Melting point: 213°–215° C.

$C_{32}H_{28}N_4O_2$ (500.60) Calculated: C 76.78 H 5.64 N 11.19 Found: 76.61 5.64 10.94

EXAMPLE 79

4'-[[2-n-Propyl-6-(2-oxo-piperidin-1-yl)-benzimidazol-1-yl]-methyl]-2-(1H-tetrazol-5-yl)-biphenyl Within 10 minutes, 155 mg (1.0 mMol) of 5-chloro-valeric acid chloride, dissolved in 5 ml of tetrahydrofuran, are added dropwise to a solution of 650 mg (1.0 mMol) of 4'-[(2-n-propyl-6-amino-benzimidazol-1-yl)-methyl]-2-(1H-triphenylmethyl-tetrazol-5-yl)-biphenyl in 30 ml of tetrahydrofuran and the mixture is stirred for a further hour at ambient temperature, then evaporated to dryness. The residue is stirred into 20 ml of ethanol, then a solution of 2.0 mMol of sodium ethoxide in 20 ml of ethanol is added and the resulting mixture is refluxed for one hour. After cooling, 10 ml of methanolic hydrochloric acid are added dropwise, the mixture is stirred for a further two hours at ambient temperature and then evaporated down. The residue is mixed with 10 ml of water and made alkaline with concentrated ammonia, whereupon the product goes into solution. By acidifying with glacial acetic acid the crude product is precipitated and then purified by column chromatography (70 g silica gel, eluant: methylene chloride+5% ethanol).

Yield: 54 mg (11% of theory),
Melting point: sintering from 117° C.
$C_{29}H_{29}N_7O$ (491.60) Calculated: C 70.85 H 5.95 N 19.95 Found: 70.69 5.94 19.99

The following compounds are obtained analogously:

4'-[[2-n-butyl-6-(2-oxo-piperidin-1-yl)-benzimidazol-1-yl]methyl]-2-(1H-tetrazol-5-yl)-biphenyl
Yield: 16% of theory,
Melting point: amorphous
$C_{30}H_{31}N_7O$ (505.63) Calculated: C 67.94 H 6.23 N 17.33 Found: 67.81 6.29 17.18

4'-[[2-n-butyl-6-(2-oxo-pyrrolidin-1-yl)-benzimidazol-1-yl]methyl]-2-(1H-tetrazol-5-yl)-biphenyl
Yield: 9% of theory,
Melting point: 150°–151° C.
$C_{29}H_{29}N_7O$ (491.60) Calculated: C 70.85 H 5.95 N 19.95 Found: 70.61 6.08 19.80

EXAMPLE 80

4'-[[2-n-Butyl-6-(propanesultam-1-yl)-benzimidazol-1-yl]-methyl]-2-(1H-tetrazol-5-yl)-biphenyl Within 10 minutes, a solution of 265 mg (1.5 mMol) of 3-chloro-propanesulphonic acid chloride in 5 ml of tetrahydrofuran is added dropwise to a solution of 665 mg (1.0 mMol) of 4'-[(2-n-butyl-6-aminobenzimidazol-1-yl)-methyl]-2-(1-triphenylmethyl-tetrazol-5-yl)-biphenyl and 1 ml of triethylamine in 30 ml of tetrahydrofuran and the mixture is stirred for 1½ hours at ambient temperature. The mixture is then evaporated to dryness, the residue is taken up in 20 ml of ethanol, a solution of 3.0 mMol of sodium ethoxide in 20 ml of ethanol is added and the resulting mixture is refluxed for two hours. After cooling, 10 ml of methanolic hydrochloric acid are added dropwise, the mixture is stirred for a further two hours at ambient temperature and finally concentrated by evaporation. The residue is mixed with 10 ml of water and brought into solution with concentrated ammonia. By acidifying with glacial acetic acid, the crude product is precipitated and then purified by column chromatography (70 g of silica gel, eluant: methylene chloride+5% ethanol).

Yield: 68.5 mg (13% of theory),
Melting point: 202°–205° C.
$C_{28}H_{29}N_7O_2S$ (527.70) Calculated: C 63.73 H 5.54 N 18.58 Found: 63.70 5.61 18.35

The following compounds are obtained analogously:

4'-[[2-n-butyl-6-(butanesultam-1-yl)-benzimidazol-1-yl]methyl]-2-(1H-tetrazol-5-yl)-biphenyl
Yield: 10% of theory,
Melting point: 185°–187° C.
$C_{29}H_{31}N_7O_2S$ (541.70) Calculated: C 64.30 H 5.95 N 18.10 Found: 64.19 5.91 17.92

4'-[[2-n-propyl-6-(butanesultam-1-yl)-benzimidazol-1-yl]methyl]-2-(1H-tetrazol-5-yl)-biphenyl
Yield: 17% of theory,
Melting point: 203°–205° C.
$C_{28}H_{29}N_7O_2S$ (527.63) Calculated: C 63.73 H 5.54 N 18.58 Found: 63.63 5.54 18.39

EXAMPLE 81

4'-[[2-n-Butyl-6-(1-benzyl-imidazolidin-2,4-dion-3-yl)-benzimidazol-1-yl]methyl]biphenyl-2-carboxylic acid trifluoroacetate Prepared analogously to Example 1 from tert.-butyl 4'-[[2-n-butyl-6-(1-benzyl-imidazolidin-2,4-dion-3-yl)-benzimidazol-1-yl]methyl]biphenyl-2-carboxylate and trifluoroacetic acid in methylene chloride.

Yield: 58% of theory,
Melting point: amorphous
$C_{35}H_{32}N_4O_4 \times CF_3COOH$ (686.71) Calculated: C 64.72 H 4.84 N 8.16 Found: 64.48 4.68 8.09

EXAMPLE 82

4'-[[2-n-Propyl-6-(5,5-pentamethylene-imidazolidin-2,4-dion-3-yl)-benzimidazol-1-yl]methyl]biphenyl-2-carboxylic acid Prepared analogously to Example 1 from tert.-butyl 4'-[[2-n-propyl-6-(5,5-pentamethylene-imidazolidin-2,4-dion-3-yl)-benzimidazol-1-yl]methyl]biphenyl-2-carboxylate and trifluoroacetic acid in methylene chloride.

Yield: 27% of theory,
Melting point: amorphous
$C_{33}H_{34}N_4O_4$ (550.63) Calculated: C 71.98 H 6.22 N 10.18 Found: 71.93 6.16 10.09

$R_f$ value: 0.60 (silica gel; eluant: methylene chloride/ethanol=9:1)

EXAMPLE 83

4'-[[2-Ethyl-6-(2-oxo-piperidin-1-yl)-benzimidazol-1-yl]-methyl]-2-(1H-tetrazol-5-yl)-biphenyl Prepared analogously to Example 41 from 4'-[[2-ethyl-6-(2-oxo-piperidin-1-yl)-benzimidazol-1-yl]methyl]-biphenyl-2-carboxylic acid nitrile and sodium azide in dimethylformamide.

Yield: 33% of theory,
Melting point: sintering from 150° C.
$C_{28}H_{27}N_7O$ (477.58) Calculated: C 70.42 H 5.70 N 20.53 Found: 70.48 5.72 19.88

EXAMPLE 84

4'-[[2-Ethyl-6-(butanesultam-1-yl)-benzimidazol-1-yl]methyl]-2-(1H-tetrazol-5-yl)-biphenyl Prepared analogously to Example 41 from 4'-[[2-ethyl-6-(butanesultam-1-yl)-benzimidazol-1-yl]methyl]biphenyl-2-carboxylic acid nitrile and sodium azide in dimethylformamide.

Yield: 36% of theory,
Melting point: decomposition from 240° C.
$C_{27}H_{27}N_7O_2S$ (513.6 4) Calculated: C 63.14 H 5.30 N 19.09 Found: 63.06 5.19 19.08

EXAMPLE 85

4'-[[2-n-Propyl-6-(3-n-hexyl-imidazo[4,5-b]pyridin-2-yl)-benzimidazol-1-yl]methyl]biphenyl-2-carboxylic acid Prepared analogously to Example 1 from tert.-butyl 4'-[[2-n-propyl-6-(3-n-hexyl-imidazo[4,5-b]pyridin-2-yl)-benzimidazol-1-yl]methyl]biphenyl-2-carboxylate and trifluoroacetic acid in methylene chloride.

Yield: 57% of theory,
Melting point: amorphous
$C_{36}H_{37}N_5O_2$ (571.74) Calculated: C 75.63 H 6.52 N 12.25 Found: 75.58 6.48 12.08

EXAMPLE 86

4'-[[2-n-Propyl-6-(3-methyl-imidazo[4,5-b]pyridin-2-yl)-benzimidazol-1-yl]methyl]biphenyl-2-carboxylic acid Prepared analogously to Example 1 from tert.-butyl 4'-[[2-n-propyl-6-(3-methyl-imidazo[4,5-b]pyridin-2-yl)-benzimidazol-1-yl]methyl]biphenyl-2-carboxylate and trifluoroacetic acid in methylene chloride.

Yield: 40% of theory,
Melting point: 208°–210° C.

$C_{31}H_{27}H_5O_2$ (501.60) Calculated: C 74.23 H 5.43 N 13.96 Found: 74.19 5.32 13.94

EXAMPLE 87

4'-[[2-n-Propyl-6-(1-methyl-imidazolin-2-yl)-benzimidazol-1-yl]methyl]biphenyl-2-carboxylic acid Prepared analogously to Example 1 from tert.-butyl 4'-[[2-n-propyl-6-(1-methyl-imidazolin-2-yl)-benzimidazol-1-yl]methyl]biphenyl-2-carboxylate and trifluoroacetic acid in methylene chloride.

Yield: 53% of theory,
Melting point: amorphous $C_{28}H_{28}N_4O_2$ (452.57) Calculated: C 74.31 H 6.24 N 12.38 Found: 74.31 6.11 12.27

The following compounds are obtained analogously to Example 87:

4'-[[2-n-butyl-6-(1-methyl-imidazolin-2-yl)-benzimidazol-1-yl]methyl]biphenyl-2-carboxylic acid 4'-[[2-n-propyl-6-(1-n-hexyl-imidazolin-2-yl)-benzimidazol-1-yl]methyl]biphenyl-2-carboxylic acid 4'-[[2-n-butyl-6-(1-n-butyl-imidazolin-2-yl)-benzimidazol-1-yl]methyl]biphenyl-2-carboxylic acid 4'-[[2-n-propyl-6-(1-cyclopropyl-imidazolin-2-yl)-benzimidazol-1-yl]methyl]biphenyl-2-carboxylic acid 4'-[[2-n-propyl-6-(1-cyclohexyl-imidazolin-2-yl)-benzimidazol-1-yl]methyl]biphenyl-2-carboxylic acid 4'-[[2-n-propyl-6-(1-methyl-imidazol-2-yl)-benzimidazol-1-yl]methyl]biphenyl-2-carboxylic acid 4'-[[2-n-butyl-6-(1-methyl-imidazol-2-yl)-benzimidazol-1-yl]methyl]biphenyl-2-carboxylic acid 4'-[[2-n-propyl-6-(1-n-hexyl-imidazol-2-yl)-benzimidazol-1-yl]methyl]biphenyl-2-carboxylic acid 4'-[[2-n-butyl-6-(1-n-butyl-imidazol-2-yl)-benzimidazol-1-yl]methyl]biphenyl-2-carboxylic acid 4'-[[2-n-propyl-6-(1-cyclopropyl-imidazol-2-yl)-benzimidazol-1-yl]methyl]biphenyl-2-carboxylic acid 4'-[[2-n-propyl-6-(1-cyclohexyl-imidazol-2-yl)-benzimidazol-1-yl]methyl]biphenyl-2-carboxylic acid

EXAMPLE 88

4'-[[2-n-Propyl-6-(1,5-dimethyl-benzimidazol-2-yl)-benzimidazol-1-yl]methyl]biphenyl-2-carboxylic acid Prepared analogously to Example 1 from tert.-butyl 4'-[[2-n-propyl-6-(1,5-dimethyl-benzimidazol-2-yl)-benzimidazol-1-yl]methyl]biphenyl-2-carboxylate and trifluoroacetic acid in methylene chloride.

Yield: 48% of theory,
Melting point: 256°–258° C.

$C_{33}H_{30}N_4O_2$ (514.63) Calculated: C 77.02 H 5.88 N 10.89 Found: 76.91 5.83 10.72

EXAMPLE 89

4'-[[2-n-Propyl-6-(1-methyl-5-trifluoromethyl-benzimidazol-2-yl)-benzimidazol-1-yl]methyl]biphenyl-2-carboxylic acid Prepared analogously to Example 1 from tert.-butyl 4'-[[2-n-propyl-6-(1-methyl-5-trifluoromethyl-benzimidazol-2-yl)-benzimidazol-1-yl]methyl]biphenyl-2-carboxylate and trifluoroacetic acid in methylene chloride.

Yield: 56% of theory,
Melting point: 183°–186° C.

$C_{33}H_{27}F_3N_4O_2$ (568.61) Calculated: C 69.71 H 4.79 N 9.85 Found: 69.58 4.72 9.80

EXAMPLE 90

4'-[[2-n-Propyl-6-(5-methyl-imidazolidin-2,4-dion-3-yl)-benzimidazol-1-yl]methyl]biphenyl-2-carboxylic acid Prepared analogously to Example 1 from tert.-butyl 4'-[[2-n-propyl-6-(5-methyl-imidazolidin-2,4-dion-3-yl)-benzimidazol-1-yl]methyl]biphenyl-2-carboxylate and trifluoroacetic acid in methylene chloride.

Yield: 29% of theory,
Melting point: amorphous $C_{28}H_{26}N_4O_4$ (482.55) Calculated: C 69.69 H 5.43 N 11.61 Found: 69.67 5.40 11.55

EXAMPLE 91

4'-[(2-n-Propyl-6-(1-methyl-imidazolidin-2,4-dion-3-yl)-benzimidazol-1-yl)-methyl]biphenyl-2-carboxylic acid Prepared analogously to Example 1 from tert.-butyl 4'-[(2-n-propyl-6-(1-methyl-imidazolidin-2,4-dion-3-yl)-benzimidazol-1-yl)-methyl]biphenyl-2-carboxylate and trifluoroacetic acid in methylene chloride.

Yield: 32% of theory,
Melting point: amorphous $C_{28}H_{26}N_4O_4$ (482.55) Calculated: C 69.69 H 5.43 N 11.61 Found: 69.61 5.38 11.49

EXAMPLE 92

4'-[(2-n-Propyl-6-(1-butyl-benzimidazol-2-yl)-benzimidazol-1-yl)-methyl]biphenyl-2-carboxylic acid Prepared analogously to Example 1 from tert.-butyl 4'-[(2-n-propyl-6-(1-butyl-benzimidazol-2-yl)-benzimidazol-1-yl)-methyl]biphenyl-2-carboxylate and trifluoroacetic acid in methylene chloride.

Yield: 59% of theory,
Melting point: sintering from 149° C.

$C_{35}H_{34}N_4O_2$ (542.69) Calculated: C 77.46 H 6.32 N 10.32 Found: 77.37 6.31 10.35

EXAMPLE 93

4'-[(2-n-Butyl-6-(1H-benzimidazol-2-yl)-benzimidazol-1-yl)methyl]biphenyl-2-carboxylic acid Prepared analogously to Example 1 from tert.-butyl 4'-[(2-n-butyl-6-(1H-benzimidazol-2-yl)-benzimidazol-1-yl)-methyl]biphenyl-2-carboxylate and trifluoroacetic acid in methylene chloride.

Yield: 62% of theory,
Melting point: 200°–202° C.

$C_{32}H_{28}N_4O_2$ (500.61) Calculated: C 76.78 H 5.64 N 11.19 Found: 76.54 5.60 11.16

EXAMPLE 94

4'-[(2-n-Butyl-6-hexahydrohomophthalimino-benzimidazol-1-yl)methyl]biphenyl-2-carboxylic acid 0.4 g (0.64 mMol) of tert.-butyl 4'-[(2-n-butyl-6-(2-carboxy-cyclohexylmethylcarbonylamino)-benzimidazol-1- yl)-methyl]biphenyl-2-carboxylate are refluxed for 1½ hours with stirring in 5 ml of phosphorus oxychloride. After cooling, the mixture is poured onto ice water and the crude product precipitated is removed by suction filtering. This is dissolved in ethanol/water, made alkaline with ammonia and concentrated in vacuo until it crystallises out. It is then suction filtered, washed with water and dried in vacuo at 120° C.

Yield: 0.15 g (42.8% of theory),

Melting point: 241°–243° C.

$C_{34}H_{35}N_3O_4$ (549.66) Calculated: C 74.29 H 6.49 N 7.64 Found: 74.14 6.64 7.81

EXAMPLE 95

4'-[(2-n-Butyl-6-(7-nitro-benzofurazan-4-yl-amino)-benzimidazol-1-yl)-methyl]biphenyl-2-carboxylic acid Prepared from 4'-[(6-amino-2-n-butyl-benzimidazol-1-yl)methyl]biphenyl-2-carboxylic acid and 4-chloro-7-nitrobenzofurazan in pyridine at ambient temperature.

Yield: 13.1% of theory, $R_f$ value: 0.75 (silica gel, methylene chloride/ethanol= 9:1)

$C_{31}H_{26}N_6O_5$ (562.58) Calculated: C 66.18 H 4.66 N 14.93 Found: 66.35 4.76 15.13

EXAMPLE 96

4'-[[2-Ethyl-6-(pyrrolidinocarbonylamino)-benzimidazol-1-yl]methyl]biphenyl-2-carboxylic acid-trifluoroacetate-semihydrate Prepared analogously to Example 1 from tert.-butyl 4'-[[2-ethyl-6-(pyrrolidinocarbonylamino)-benzimidazol-1-yl]-methyl]biphenyl-2-carboxylate and trifluoroacetic acid in methylene chloride.

Yield: 80.9% of theory,

Melting point: 178°–179° C.

$C_{28}H_{28}N_4O_3 \times CF_3COOH \times 0.5\ H_2O$ (591.59) Calculated: C 60.90 H 5.11 N 9.47 Found: 61.10 5.22 9.26

$R_f$ value: 0.48 (silica gel; ethyl acetate/ethanol/ammonia= 50:45:5)

EXAMPLE 97

4'-[[2-Methyl-6-(pyrrolidinocarbonylamino)-benzimidazol-1-yl]methyl]biphenyl-2-carboxylic acid-trifluoroacetate Prepared analogously to Example 1 from tert.-butyl 4'-[[2-methyl-6-(pyrrolidinocarbonylamino)-benzimidazol-1-yl]-methyl]biphenyl-2-carboxylate and trifluoroacetic acid in methylene chloride.

Yield: 82.1% of theory,

Melting point: 181°–182° C.

$C_{27}H_{26}N_4O_3 \times CF_3COOH$ (568.55) Calculated: C 61.26 H 4.79 N 9.85 Found: 60.99 5.09 9.89

$R_f$ value: 0.38 (silica gel; ethyl acetate/ethanol/ammonia= 50:45:5)

EXAMPLE 98

4'-[[2-n-Propyl-6-(pyrrolidinocarbonylamino)-benzimidazol-1-yl]methyl]biphenyl-2-carboxylic acid-trifluoroacetate Prepared analogously to Example 1 from tert.-butyl 4'-[[2-n-propyl-6-(pyrrolidinocarbonylamino)-benzimidazol-1-yl]methyl]biphenyl-2-carboxylate and trifluoroacetic acid in methylene chloride.

Yield: 79.7% of theory,

Melting point: 207°–208° C.

$C_{29}H_{30}N_4O_3 \times CF_3COOH$ (596.61) Calculated: C 62.41 H 5.24 N 9.39 Found: 62.38 5.36 9.42

$R_f$ value: 0.55 (silica gel; ethyl acetate/ethanol/ammonia= 50:45:5)

EXAMPLE 99

4'-[[2-Methylmercapto-6-(pyrrolidinocarbonylamino)-benzimidazol-1-yl] methyl]biphenyl-2-carboxylic acid-trifluoroacetate Prepared analogously to Example 1 from tert.-butyl 4'-[[2-methylmercapto-6-(pyrrolidinocarbonylamino)-benzimidazol-1-yl]methyl]biphenyl-2-carboxylate and trifluoroacetic acid in methylene chloride.

Yield: 96.1% of theory,

Melting point: 177°–178° C.

$C_{27}H_{26}N_4O_3S \times CF_3COOH$ (600.61) Calculated: C 57.99 H 4.53 N 9.33 Found: 57.68 4.75 9.30

$R_f$ value: 0.52 (silica gel; ethyl acetate/ethanol/ammonia= 50:45:5)

EXAMPLE 100

4'-[[6-(2,3-Dimethylmaleic acid imido)-2-methylmercapto-benzimidazol-1-yl]methyl] biphenyl-2-carboxylic acid Prepared analogously to Example 1 from tert.-butyl 4'-[[6-(2,3-dimethylmaleic acid imido)-2-methylmercapto-benzimidazol-1-yl]methyl]biphenyl-2-carboxylate and trifluoroacetic acid in methylene chloride.

Yield: 91.7% of theory,

Melting point: 276°–277° C.

$C_{28}H_{23}N_3O_4S$ (497.57) Calculated: C 67.59 H 4.66 N 8.45 S 6.44 Found: 67.57 4.94 8.40 6.37

$R_f$ value: 0.47 (silica gel; ethyl acetate/ethanol/ammonia= 50:45:5)

EXAMPLE 101

4'-[[2-n-Butyl-6-[3-(7-nitrobenzofurazan-4-yl-amino)-propionylamino]benzimidazol-1-yl]methyl]-2-(1H-tetrazol-5-yl)-biphenyl-hydrate Prepared analogously to Example 55 from 4'-[[2-n-butyl-6-[3-(7-nitrobenzofurazan-4-yl-amino)-propionylamino]-benzimidazol-1-yl]methyl]-2-(1-triphenylmethyl-tetrazol-5-yl)-biphenyl and 2N hydrochloric acid in ethanol.

Yield: 33.3% of theory,

Melting point: 179°–181° C.

$C_{34}H_{31}N_{11}O_4 \times H_2O$ (675.70) Calculated: C 60.43 H 4.92 N 22.80 Found: 60.24 5.09 22.69

EXAMPLE 102

4'-[[2-n-Butyl-6-[3-(7-nitrobenzofurazan-4-yl-amino)-propionylamino]benzimidazol-1-yl]methyl] biphenyl-2-carboxylic acid-trifluoroacetate-hydrate Prepared analogously to Example 1 from tert.-butyl 4'-[[2-n-butyl-6-[3-(7-nitrobenzofurazan-4-yl-amino)-propionylamino]benzimidazol-1-yl]methyl]biphenyl-2-carboxylate and trifluoroacetic acid in methylene chloride.

Yield: 87.5% of theory,

Melting point: 127° C. (decomp.)

$C_{34}H_{31}N_7O_6 \times CF_3COOH \times H_2O$ (765.69) Calculated: C 56.47 H 4.47 N 12.80 Found: 56.68 4.27 12.67

EXAMPLE 103

4'-[[6-(2,3-Dimethylmaleic acid imido)-2-methyl-benzimidazol-1-yl]methyl]biphenyl-2-carboxylic acid Prepared analogously to Example 1 from tert.-butyl 4'-[[6-(2,3-dimethylmaleic acid imido)-2-methyl-benzimidazol-1-yl]methyl]biphenyl-2-carboxylate and trifluoroacetic acid in methylene chloride.

Yield: 94.4% of theory,

Melting point: 327°–328° C.

$C_{28}H_{23}N_3O_4$ (465.51) Calculated: C 72.25 H 4.98 N 9.03 Found: 72.00 5.08 9.06

$R_f$ value: 0.33 (silica gel; ethyl acetate/ethanol/ammonia= 50:45:5)

EXAMPLE 104

4'-[[6-(2,3-Dimethylmaleic acid imido)-benzimidazol-1-yl]methyl]biphenyl-2-carboxylic acid-semihydrate Prepared analogously to Example 1 from tert.-butyl 4'-[[6-(2,3-dimethylmaleic acid imido)-benzimidazol-1-yl]methyl]biphenyl-2-carboxylate and trifluoroacetic acid in methylene chloride.

Yield: 95.5% of theory,

Melting point: 223°–224° C.

$C_{27}H_{21}N_3O_4 \times 0.5\ H_2O$ (460.49) Calculated: C 70.42 H 4.82 N 9.13 Found: 70.30 4.88 8.81

$R_f$ value: 0.34 (silica gel; ethyl acetate/ethanol/ammonia= 50:45:5)

EXAMPLE 105

4'-[[6-(2,3-Dimethylmaleic acid imido)-2-n-propyl-benzimidazol-1-yl]methyl]biphenyl-2-carboxylic acid-monohydrate Prepared analogously to Example 1 from tert.-butyl 4'-[[6-(2,3-dimethylmaleic acid imido)-2-n-propyl-benzimidazol-1-yl]methyl]biphenyl-2-carboxylate and trifluoroacetic acid in methylene chloride.

Yield: 92.5% of theory,

Melting point: 309°–310° C.

$C_{30}H_{27}N_3O_4 \times H_2O$ (511.58) Calculated: C 70.44 H 5.71 N 8.21 Found: 70.44 5.64 8.19

$R_f$ value: 0.47 (silica gel; ethyl acetate/ethanol/ammonia= 50:45:5)

EXAMPLE 106

4'-[[6-(2,3-Dimethylmaleic acid imido)-2-ethyl-benzimidazol-1-yl]methyl]biphenyl-2-carboxylic acid Prepared analogously to Example 1 from tert.-butyl 4'-[[6-(2,3-dimethylmaleic acid imido)-2-ethyl-benzimidazol-1-yl]methyl]biphenyl-2-carboxylate and trifluoroacetic acid in methylene chloride.

Yield: 87.5% of theory,

Melting point: 307°–308° C.

$C_{29}H_{25}N_3O_4$ (479.53) Calculated: C 72.64 H 5.25 N 8.76 Found: 72.41 5.37 8.94

$R_f$ value: 0.40 (silica gel; ethyl acetate/ethanol/ammonia= 50:45:5)

EXAMPLE 107

4'-[[2-Ethyl-6-(1-methylbenzimidazol-2-yl)-benzimidazol-1-yl]methyl]biphenyl-2-carboxylic acid Prepared analogously to Example 1 from tert.-butyl 4'-[[2-ethyl-6-(1-methyl-benzimidazol-2-yl)-benzimidazol-1-yl]methyl]biphenyl-2-carboxylate and trifluoroacetic acid in methylene chloride.

Yield: 31% of theory,

Melting point: 183°–185° C.

$C_{31}H_{26}N_4O_2$ (486.60) Calculated: C 76.52 H 5.39 N 11.52 Found: 76.73 5.49 11.70

EXAMPLE 108

4'-[[2-Methyl-6-(butanesultam-1-yl)-benzimidazol-1-yl]methyl]-2-(1H-tetrazol-5-yl)-biphenyl Prepared analogously to Example 41 from 4'-[[2-methyl-6-(butanesultam-1-yl)-benzimidazol-1-yl]methyl]-2-cyano-biphenyl and sodium azide in dimethylformamide.

Yield: 27% of theory,

Melting point: 173°–175° C.

$C_2H_{25}N_7O_2S$ (499.60) Calculated: C 62.51 H 5.04 N 19.63 S 6.42 Found: 62.39 5.05 19.44 6.33

Mass spectrum: m/e=499

EXAMPLE 109

4'-[[2-Methyl-6-(1-methylbenzimidazol-2-yl)-benzimidazol-1-yl]methyl]-2-(1H-tetrazol-5-yl)-biphenyl Prepared analogously to Example 41 from 4'-[[2-methyl-6-(1-methylbenzimidazol-2-yl)-benzimidazol-1-yl]methyl]-2-cyano-biphenyl and sodium azide in dimethylformamide.

Yield: 26.5% of theory,

Melting point: 214°–217° C.

$C_{30}H_{24}N_8$ (496.80) Calculated: C 72.56 H 4.87 N 22.56 Found: 72.32 5.01 22.23

EXAMPLE 110

4'-[[6-(Butanesultam-1-yl)-benzimidazol-1-yl]methyl]-2-(1H-tetrazol-5-yl)-biphenyl Prepared analogously to Example 41 from 4'-[[6-(butanesultam-1-yl)-benzimidazol-1-yl]methyl]-2-cyano-biphenyl and sodium azide in dimethylformamide.

Yield: 60.0% of theory,

Melting point: 246°–249° C.

$C_{25}H_{23}N_7O_2S$ (485.60) Calculated: C 61.84 H 4.77 N 20.19 Found: 61.75 4.92 20.28

EXAMPLE 111

4'-[[2-Ethyl-6-(1-methylbenzimidazol-2-yl)-benzimidazol-1-yl]methyl]-2-(1H-tetrazol-5-yl)-biphenyl Prepared analogously to Example 41 from 4'-[[2-ethyl-6-(1-methyl-benzimidazol-2-yl)-benzimidazol-1-yl]methyl]-2-cyano-biphenyl and sodium azide in dimethylformamide.

Yield: 41.0% of theory,
Melting point: from 178° C. (sintering)
$C_{31}H_{26}N_8$ (510.60) Calculated: C 72.92 H 5.13 N 21.95
Found: 72.94 5.25 21.71
Mass spectrum: m/e=510

EXAMPLE 122

4'-[[2-Ethyl-6-(N-benzenesulphonyl-methylamino)-benzimidazol-1-yl]methyl]-2-(1H-tetrazol-5-yl)-biphenyl Prepared analogously to Example 41 from 4'-[[2-ethyl-6-(N-benzenesulphonyl-methylamino)-benzimidazol-1-yl]methyl]-2-cyano-biphenyl and sodium azide in dimethylformamide.
Yield: 66.0% of theory,
Melting point: 226°–228° C.
$C_{30}H_{27}N_7O_2S$ (549.70) Calculated: C 65.55 H 4.95 N 17.84 S 5.83 Found: 65.38 4.95 17.59 5.79

EXAMPLE 113

4'-[[2-n-Propyl-6-(N-benzenesulphonyl-methylamino)-benzimidazol-1-yl]methyl]-2-(1H-tetrazol-5-yl)-biphenyl Prepared analogously to Example 41 from 4'-[[2-n-propyl-6-(N-benzenesulphonyl-methylamino)-benzimidazol-1-yl]methyl]-2-cyano-biphenyl and sodium azide in dimethylformamide.
Yield: 83.4% of theory,
Melting point: 177°–179° C.
$C_{31}H_{29}N_7O_2S$ (563.70) Calculated: C 66.05 H 5.18 N 17.40 S 5.69 Found: 65.89 5.14 17.21 5.73

EXAMPLE 114

4'-[(2-n-Butyl-6-benzenesulphonyloxy-benzimidazol-1-yl)-methyl]biphenyl-2-carboxylic acid Prepared analogously to Example 1 from tert.-butyl 4'-[(2-n-butyl-6-benzenesulphonyloxy-benzimidazol-1-yl)-methyl]biphenyl-2-carboxylate and trifluoroacetic acid in methylene chloride.
Yield: 8.2% of theory,
Melting point: 193°–195° C.
$C_{31}H_{28}N_2O_5S$ (540.60) Calculated: C 68.92 H 5.22 N 5.18 Found: 68.94 5.08 5.08

EXAMPLE 115

4'-[[2-n-Butyl-6-(3-benzyl-3,4,5,6-tetrahydro-2(1H)-pyrimidinon-1-yl)-benzimidazol-1yl]methyl]-2-(1H-tetrazol-5-yl)-biphenyl Prepared analogously to Example 55 from 4'-[[2-n-butyl-6-(3-benzyl-3,4,5,6-tetrahydro-2(1H)-pyrimidinon-1-yl)-benzimidazol-1-yl]methyl]-2-(1-triphenylmethyl-tetrazol-5-yl)-biphenyl and methanol in methanolic hydrochloric acid.
Yield: 28.0% of theory,
Melting point: from 125° C. (decomp.)
$C_{36}H_{36}N_8O$ (596.80) Calculated: C 72.46 H 6.08 N 18.78
Found: 72.26 5.94 18.85

EXAMPLE 116

4'-[[2-n-Butyl-5-(3-benzyl-3,4,5,6-tetrahydro-2(1H)-pyrimidinon-1-yl)-benzimidazol-1-yl]-methyl]-2-(1H-tetrazol-5-yl)-biphenyl Prepared analogously to Example 55 from 4'-[[2-n-butyl-5-(3-benzyl-3,4,5,6-tetrahydro-2(1H)-pyrimidinon-1-yl)-benzimidazol-1-yl]methyl]-2-(1-triphenylmethyl-tetrazol-5-yl)-biphenyl and methanol in methanolic hydrochloric acid.
Yield: 31.0% of theory,
Melting point: from 125° C. (decomp.)
$C_{36}H_{36}N_8O$ (596.80) Calculated: C 72.46 H 6.08 N 38.78
Found: 72.27 6.03 18.61

EXAMPLE 117

4'-[[2-n-Propyl-6-(3-benzyl-3,4,5,6-tetrahydro-2(1H)-pyrimidinon-1-yl)-benzimidazol-1-yl]methyl]-2 (1H-tetrazol-5-yl)-biphenyl Prepared analogously to Example 55 from 4'-[[2-n-propyl-6-(3-benzyl-3,4,5,6-tetrahydro-2(1H)-pyrimidinon-1-yl)-benzimidazol-1-yl]methyl]-2-(1-triphenylmethyl-tetrazol-5-yl)-biphenyl and methanol in methanolic hydrochloric acid.
Yield: 35.0% of theory,
Melting point: from 132° C. (decomp.)
$C_{35}H_{34}N_8O$ (582.71) Calculated: C 72.14 H 5.88 N 19.23
Found: 71.98 6.02 19.11

EXAMPLE 118

4'-[[2-Ethyl-6-(3-benzyl-3,4,5,6-tetrahydro-2(1H)-pyrimidinon-1-yl)-benzimidazol-1-yl]methyl]-2-(1H-tetrazol-5-yl)-biphenyl Prepared analogously to Example 55 from 4'-[[2-ethyl-6-(3-benzyl-3,4,5,6-tetrahydro-2(1H)-pyrimidinon-1-yl)-benzimidazol-1-yl]methyl]-2-(1-triphenylmethyl-tetrazol-5-yl)-biphenyl and methanol in methanolic hydrochloric acid.
Yield: 22.0% of theory,
Melting point: from 106° C. (decomp.)
$C_{34}H_{32}N_8O$ (568.68) Calculated: C 71.81 H 5.67 N 19.70
Found: 71.73 5.54 19.92

EXAMPLE 119

4'-[[2-n-Butyl-6-(4,5-dihydro-2H-pyridazin-3-on-6-yl)-benzimidazol-1-yl]methyl]biphenyl-2-carboxylic acid Prepared analogously to Example 64 from methyl 4'-[[2-n-butyl-6-(4,5-dihydro-2H-pyridazin-3-on-6-yl)-benzimidazol-1-yl]methyl]biphenyl-2-carboxylate and sodium hydroxide solution in ethanol.
Yield: 80.0% of theory,
Melting point: 276°–283° C.
$C_{29}H_{28}N_4O_3$ (480.60) Calculated: C 72.48 H 5.87 N 11.66 Found: 72.20 6.13 11.53
Mass spectrum: m/e=480

The following compounds are obtained analogously to Example 119:
4'-[[2-ethyl-6-(2H-pyridazin-3-on-6-yl)-benzimidazol-1-yl]methyl]biphenyl-2-carboxylic acid
4'-[[2-n-propyl-6-(2H-pyridazin-3-on-6-yl)-benzimidazol-1-yl]methyl]biphenyl-2-carboxylic acid
4'-[[2-n-butyl-6-(2H-pyridazin-3-on-6-yl)-benzimidazol-1-yl]methyl]biphenyl-2-carboxylic acid
4'-[[2-n-propyl-6-(2-methyl-4,5-dihydro-pyridazin-3-on-6-yl)-benzimidazol-1-yl]methyl]biphenyl-2-carboxylic acid
4'-[[2-n-propyl-6-(2-benzyl-4,5-dihydro-pyridazin-3-on-6-yl)-benzimidazol-1-yl]methyl]biphenyl-2-carboxylic acid

EXAMPLE 120

4'-[[2-n-Propyl-6-(4,5-dihydro-2H-pyridazin-3-on-6-yl)-benzimidazol-1-yl]methyl]biphenyl-2-carboxylic acid Prepared analogously to Example 64 from methyl 4'-[[2-n-propyl-6-(4,5-dihydro-2H-pyridazin-3-on-6-yl)- benzimidazol-1-yl]methyl]biphenyl-2-carboxylate and sodium hydroxide solution in ethanol.

Yield: 66.0% of theory,

Melting point: 236°–241° C.

$C_{28}H_{26}N_4O_3$ (466.54) Calculated: C 72.09 H 5.62 N 12.01 Found: 71.88 5.61 11.95

EXAMPLE 121

4'-[[2-Ethyl-6-(4,5-dihydro-2H-pyridazin-3-on-6-yl)-benzimidazol-1-yl]methyl]biphenyl-2-carboxylic acid Prepared analogously to Example 64 from methyl 4'-[[2-ethyl-6-(4,5-dihydro-2H-pyridazin-3-on-6-yl)-benzimidazol-1-yl]methyl]biphenyl-2-carboxylate and sodium hydroxide solution in ethanol.

Yield: 71.0% of theory,

Melting point: 255°–257° C.

$C_{27}H_{24}N_4O_3$ (452.51) Calculated: C 71.67 H 5.35 N 12.38 Found: 71.41 5.51 12.12

EXAMPLE 122

4'-[[2-n-Butyl-6-(3-cyclohexyl-propylamino)-benzimidazol-1-yl]methyl]biphenyl-2-carboxylic acid Prepared analogously to Example 1 from tert.-butyl 4'-[[2-n-butyl-6-(3-cyclohexyl-propylamino)-benzimidazol-1-yl]methyl]biphenyl-2-carboxylate and trifluoroacetic acid in methylene chloride.

Yield: 85.7% of theory,

Melting point: 152°–153° C.

$C_{34}H_{11}N_3O_2 \times 0.75$ $CF_3COOH$ (609.24) Calculated: C 69.99 H 6.91 N 6.90 Found: 70.02 6.93 6.84

$R_f$ value: 0.24 (silica gel; ethyl acetate/ethanol/ammonia= 80:40:2)

In the Examples of Pharmaceutical Formulations which follow, any suitable compound of formula I, particularly compounds A to L of the pharmacological test report, may be used as the active substance:

Example I

| Ampoules containing 50 mg of active substance per 5 ml | |
|---|---|
| Active substance | 50 mg |
| $KH_2PO_4$ | 2 mg |
| $Na_2HPO_4 \times 2H_2O$ | 50 mg |
| NaCl | 12 mg |
| Water for injections ad | 5 ml |

Preparation:

The buffer substances and isotonic substance are dissolved in some of the water. The active substance is added and, once it has been completely dissolved, water is added to make up the required volume.

Example II

| Ampoules containing 100 mg of active substance per 5 ml | |
|---|---|
| Active substance | 100 mg |
| Methyl glucamine | 35 mg |
| Glycofurol | 1000 mg |
| Polyethyleneglycol-polypropylene-glycol block polymer | 250 mg |
| Water for injections ad | 5 ml |

Preparation:

Methyl glucamine is dissolved in some of the water and the active substance is dissolved with stirring and heating. After the addition of solvents, water is added to make up the desired volume.

Example III

| Tablets containing 50 mg of active substance | |
|---|---|
| Active substance | 50.0 mg |
| Calcium phosphate | 70.0 mg |
| Lactose | 40.0 mg |
| Corn starch | 35.0 mg |
| Polyvinylpyrrolidone | 3.5 mg |
| Magnesium stearate | 1.5 mg |
| | 200.0 mg |

Preparation:

The active substance, $CaHPO_4$, lactose and corn starch are uniformly moistened with an aqueous PVP solution. The mass is passed through a 2 mm screen, dried at 50° C. in a circulating air dryer and screened again.

After the lubricant has been added, the granules are compressed in a tablet making machine.

Example IV

| Coated tablets containing 50 mg of active substance | |
|---|---|
| Active substance | 50.0 mg |
| Lysine | 25.0 mg |
| Lactose | 60.0 mg |
| Corn starch | 34.0 mg |
| Gelatin | 10.0 mg |
| Magnesium stearate | 1.0 mg |
| | 180.0 mg |

Preparation:

The active substance is mixed with the excipients and moistened with an aqueous gelatin solution. After screening and drying the granules are mixed with magnesium stearate and compressed to form tablet cores.

The cores thus produced are covered with a coating by known methods. A colouring may be added to the coating suspension or solution.

Example V

| Coated tablets containing 100 mg of active substance | |
|---|---|
| Active substance | 100.0 mg |
| Lysine | 50.0 mg |
| Lactose | 86.0 mg |
| Corn starch | 50.0 mg |
| Polyvinylpyrrolidone | 2.8 mg |
| Microcrystalline cellulose | 60.0 mg |

-continued

| Coated tablets containing 100 mg of active substance | |
| --- | --- |
| Magnesium stearate | 1.2 mg |
| | 350.0 mg |

Preparation:

The active substance is mixed with the excipients and moistened with an aqueous PVP solution. The moist mass is passed through a 1.5 mm screen and dried at 45° C. After drying, it is screened again and the magnesium stearate is added. This mixture is compressed into cores.

The cores thus produced are covered with a coating by known methods. Colourings may be added to the coating suspension or solution.

Example VI

| Capsules containing 250 mg of active substance | |
| --- | --- |
| Active substance | 250.0 mg |
| Corn starch | 68.5 mg |
| Magnesium stearate | 1.5 mg |
| | 320.0 mg |

Preparation:

The active substance and corn starch are mixed together and moistened with water. The moist mass is screened and dried. The dry granules are screened and mixed with magnesium stearate. The final mixture is packed into size 1 hard gelatine capsules.

Example VII

| Oral suspension containing 50 mg of active substance per 5 ml | |
| --- | --- |
| Active substance | 50.0 mg |
| Hydroxyethylcellulose | 50.0 mg |
| Sorbic acid | 5.0 mg |
| 70% sorbitol | 600.0 mg |
| Glycerol | 200.0 mg |
| Flavouring | 15.0 mg |
| Water ad | 5.0 ml |

Preparation:

Distilled water is heated to 70° C. Hydroxyethyl-cellulose is dissolved therein with stirring. By the addition of sorbitol solution and glycerol the mixture is cooled to ambient temperature. At ambient temperature, sorbic acid, flavouring and active substance are added. The suspension is evacuated with stirring to remove any air. One dose of 50 mg is contained in 5.0 ml.

Example VIII

| Suppositories containing 100 mg of active substance | |
| --- | --- |
| Active substance | 100.0 mg |
| Solid fat | 1600.0 mg |
| | 1700.0 mg |

Preparation:

The hard fat is melted. At 40° C. the ground active substance is homogeneously dispersed in the melt. It is cooled to 38° C. and poured into slightly chilled suppository moulds.

What is claimed is:

1. A method for treating hypertension in a patient which comprises administering to the patient a therapeutically effective amount of a benzimidazole of the formula I

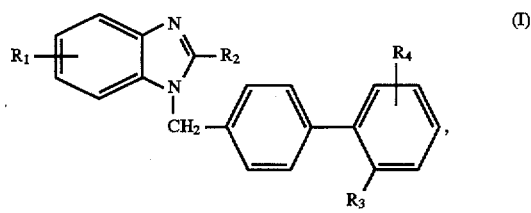

wherein $R_1$ represents a tetrahydrobenzimidazolyl group, or a benzimidazolyl group optionally substituted in the phenyl nucleus by a fluorine, chlorine or bromine atom, by a $C_{1-3}$-alkyl group, by a $C_{1-3}$-alkoxy or by a trifluoromethyl group, wherein the NH group of the above-mentioned imidazole rings may additionally be substituted by a $C_{1-6}$-alkyl group or by a $C_{3-7}$-cycloalkyl group;

$R_2$ represents a hydrogen atom or a straight-chained or branched $C_{1-5}$-alkyl group in which a methylene group may be replaced by a sulphur atom;

$R_3$ represents a carboxy, 1H-tetrazolyl or 1-triphenylmethyl-tetrazolyl group, or an alkoxycarbonyl group with a total of 2 to 5 carbon atoms; and $R_4$ represents a hydrogen, fluorine, chlorine or bromine atom;

or a pharmaceutically acceptable salt thereof.

2. The method of claim 1 wherein, in the benzimidazole of formula I or its pharmaceutically acceptable salt, $R_1$ represents a tetrahydrobenzimidazolyl group, or a benzimidazolyl group optionally substituted in the phenyl nucleus by a fluorine, chlorine or bromine atom or by a methyl, methoxy or trifluoromethyl group, wherein the NH-group of the above-mentioned imidazole rings may additionally be substituted by a $C_{1-6}$alkyl group or by a $C_{3-6}$-cycloalkyl group;

$R_2$ represents a hydrogen atom or a straight-chained or branched $C_{1-4}$alkyl group in which a methylene group may be replaced by sulphur atom;

$R_3$ represents a carboxy group, an alkoxycarbonyl group with a total of 2 to 5 carbon atoms or a 1H-tetrazolyl group; and $R_4$ represents a hydrogen, fluorine, chlorine or bromine atom.

3. The method of claim 1 wherein, in the benzimidazole of formula I or its pharmaceutically acceptable salt, claim 1, $R_1$ is in the 6-positions and represents a 1-methylbenzimidazol-2-yl group;

$R_2$ represents a methyl, ethyl, n-propyl or n-butyl group;

$R_3$ represents a carboxy or 1H-tetrazolyl group; and $R_4$ represents a hydrogen atom.

4. A method for treating hypertension in a patient which comprises administering to the patient a therapeutically effective mount of a compound selected from the group consisting of:

4'-[[2-n-propyl-6-(1-methylbenzimidazol-2-yl)-benzimidazol-1-yl]methyl]biphenyl-2-carboxylic acid, 4'-[[2-n-propyl-6-(1-methylbenzimidazol-2-yl)-benzimidazol-1-yl]methyl]-2-(1H-tetrazol-5-yl)-biphenyl, and the pharmaceutically salts thereof.

5. A benzimidazole of the formula:

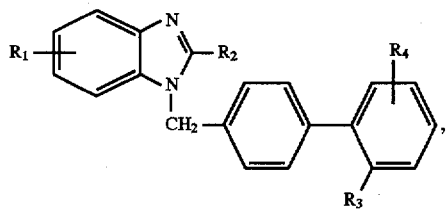

wherein
- $R_1$ represents a tetrahydrobenzimidazolyl group, or a benzimidazolyl group optionally substituted in the phenyl nucleus by a fluorine, chlorine or bromine atom, by a $C_{1-3}$-alkyl group, by a $C_{1-3}$-alkoxy or by a trifluoromethyl group, wherein the NH group of the abovementioned imidazole rings may additionally be substituted by a $C_{1-6}$-alkyl group or by a $C_{3-7}$-cycloalkyl group;
- $R_2$ represents a hydrogen atom or a straight-chained or branched $C_{1-5}$-alkyl group in which a methylene group may be replaced by a sulphur atom;
- $R_3$ represents a carboxy, 1H-tetrazolyl or 1-triphenylmethyl-tetrazolyl group, or an alkoxycarbonyl group with a total of 2 to 5 carbon atoms; and
- $R_4$ represents a hydrogen, fluorine, chlorine or bromine atom;

or a pharmaceutically acceptable salt thereof.

6. A benzimidazole as recited in claim 5, wherein
- $R_1$ represents a tetrahydrobenzimidazolyl group, or a benzimidazolyl group optionally substituted in the phenyl nucleus by a fluorine, chlorine or bromine atom or by a methyl, methoxy or trifluoromethyl group, wherein the NH-group of the above-mentioned imidazole rings may additionally be substituted by a $C_{1-6}$-alkyl group or by a $C_{3-6}$-cycloalkyl group;
- $R_2$ represents a hydrogen atom or a straight-chained or branched $C_{1-4}$-alkyl group in which a methylene group may be replaced by sulphur atom;
- $R_3$ represents a carboxy group, an alkoxycarbonyl group with a total of 2 to 5 carbon atoms or a 1H-tetrazolyl group; and
- $R_4$ represents a hydrogen, fluorine, chlorine or bromine atom;

or a pharmaceutically acceptable salt thereof.

7. A benzimidazole as recited in claim 5, wherein
- $R_1$ is in the 6-positions and represents a 1-methylbenzimidazol-2-yl group;
- $R_2$ represents a methyl, ethyl, n-propyl or n-butyl group;
- $R_3$ represents a carboxy or 1H-tetrazolyl group; and
- $R_4$ represents a hydrogen atom;

or a pharmaceutically acceptable salt thereof.

8. A compound selected from the group consisting of:
4'-[[2-n-propyl-6-(1-methylbenzimidazol-2-yl)-benzimidazol-1-yl]methyl]biphenyl-2-carboxylic acid,
4'-[[2-n-propyl-6-(1-methylbenzimidazol-2-yl)-benzimidazol-1-yl]methyl]-2-(1H-tetrazol-5-yl)-biphenyl,
and the pharmaceutically salts thereof.

* * * * *

UNITED STATES PATENT AND TRADEMARK OFFICE
CERTIFICATE OF CORRECTION

PATENT NO. : 5,684,029

DATED : November 4, 1997

INVENTOR(S) : Narr, et al

It is certified that error appears in the above-identified patent and that said Letters Patent is hereby corrected as shown below:

On the title page:
On page 1, the sentence that is indicated by the symbol "[*]" and the word "Notice", and which reads:

"The term of this patent shall not extend beyond the expiration date of Pat. No. 5,591,702."

is changed to read:

--The term of this patent shall not extend beyond the expiration date of Pat. No. 5,591,762.--

Signed and Sealed this

Twenty-seventh Day of January, 1998

Attest:

BRUCE LEHMAN

*Attesting Officer*  *Commissioner of Patents and Trademarks*